United States Patent [19]
Zatz et al.

[11] Patent Number: 4,717,713
[45] Date of Patent: Jan. 5, 1988

[54] CONTROLLED RELEASE LIQUID PHARMACEUTICAL

[75] Inventors: Joel L. Zatz, Metuchen, N.J.; David W. Woodford, Rensselaer, N.Y.

[73] Assignee: Research Corporation, New York, N.Y.

[21] Appl. No.: 546,846

[22] Filed: Oct. 31, 1983

[51] Int. Cl.⁴ .................... A61K 37/00; A61K 31/715
[52] U.S. Cl. .......................................... 514/2; 514/54; 514/57; 514/263; 514/869; 514/965; 514/929; 514/944; 514/964
[58] Field of Search ................ 424/253, 177, 180, 19; 514/263, 3, 54, 57, 869, 905, 929, 944, 964

[56] References Cited

U.S. PATENT DOCUMENTS 4,002,756  1/1977  Higuchi et al.
4,136,173  1/1979  Pramoda et al. ........................ 514/2

FOREIGN PATENT DOCUMENTS 2407720  6/1979  France .................................. 424/19

OTHER PUBLICATIONS

Barzegar-Jalali et al., "The Effect of Suspending Agents on the Release of Aspirin from Aqueous Suspensions In Vitro," Int. J. Pharm., vol. 2, p. 195-201, (1979).

Barzegar-Jalali et al., "The Effects of Various Suspending Agents on the Bioavailabilities of Aspirin and Salicyclic Acid in the Rabbit," Int. J. Pharm., vol. 3, pp. 133-141, (1979).

Remington's Pharmaceutical Sciences, 1980, Mack Pub. Co., pp. 1244-1248.

Primary Examiner—J. R. Brown
Assistant Examiner—John W. Rollins
Attorney, Agent, or Firm—Scully, Scott, Murphy & Presser

[57] ABSTRACT

A controlled release pharmaceutical composition including a solution or suspension vehicle and a pharmaceutically active agent. The composition is administered to the body in a normally liquid formulation and thereafter forms a semi-solid gel-like matrix in the environment of the stomach thereby effecting controlled release of the pharmaceutically active agent.

24 Claims, 14 Drawing Figures

THE EFFECT OF ADDITION OF 0.3 PERCENT XANTHAN GUM (KELCO SS-4749) TO A SUSPENSION CONTAINING 0.3 PERCENT EACH OF GELATIN AND CARAGEENAN ON DISSOLUTION OF 4 PERCENT THEOPHYLLINE SUSPENSIONS

CONTROLLED RELEASE LIQUID PHARMACEUTICAL

BACKGROUND OF THE INVENTION

The present invention relates to controlled release pharmaceutical compositions. More specifically, this invention is directed to compositions which include a solution or suspension vehicle and a pharmaceutically active agent which can be administered to the body in a normally liquid formulation and thereafter form a semi-solid or gel-like matrix in the environment of the stomach thereby effecting controlled release of the incorporated medicament.

Since the salient aspect of drug delivery by familiar conventional dosage forms, including tablets, capsules, eye drops and injectors is the fluctuation between high and low concentration within each interval between dosing, the pharmaceutical industry has directed much of its developmental effort to prolonging the residence time of drug molecules in the body to enhance convenience of the regimen and improve patient compliance. Moreover, certain medicants, particularly those exhibiting a short half-life which necessitate frequent dosing, are too rapidly absorbed and sometimes result in peak serum levels that are excessively high. Such circumstances often result in the development of toxic symptoms.

Thus, it is known in the pharmaceutical arts to prepare pharmaceutical compositions which may be administered by various methods, e.g., orally, topically, rectally, opthalmicly, oticly, etc. to humans and animals which provide for a delayed release of the active ingredient incorporated in the particular composition. In all of these methods the purpose and effect are the same, i.e., to provide more precise control over drug concentration in the blood or target tissue and prolonged drug activity while avoiding symptomatic side effects. Ideally, by releasing a drug in vivo according to a predictable, therapeutically rational rate or rate program, such pharmaceuticals deliver drugs systemically or to a particular target organ continuously for a specified length of time thereby programming any desired time pattern of drug release and permitting delivery at a constant rate, i.e., a rate equal to the rate of loss.

The ability to control the duration of drug release and to maintain the drug at a predictable, specified concentration in vivo offers many advantages over other forms of medication. For example, less total drug may suffice for treatment than with conventional dosage thereby eliminating harmful side effects. Such deleterious side effects may specifically include gastric irritation and erosion, e.g., the gastrointestinal bleeding that occurs with long term use of conventional forms of aspirin declines when it is administered in controlled-release form.

Several slow release formulations are well known in the art including enteric coated pellets, tablets and capsules and/or formulations wherein the active ingredients are dispersed in a medium totally insoluble in physiologic fluids or wherein the release of the active medicament is brought about by a breakdown of formulations due to mechanical means. For example, U.S. Pat. No. 4,292,299 to Suzuki, et al. discloses a slow-releasing medical preparation which is administered by adhering to the wet mucous surface of a mucous membrane and skin of humans or animals. The composition includes an adhesive polymer which swells upon moistening and a non-adhesive layer which contains the particular medicament. U.S. Pat. No. 4,235,870 to Leslie describes slow-release compositions which include a higher aliphatic alcohol in combination with certain hydrated materials such as hydrated hydroxy-alkyl cellulose in critical proportion which thereby achieves delayed and uniform release of the medicament incorporated in the composition. U.S. Pat. No. 3,493,652 to Hartman relates to a method of effecting the controlled release of pharmaceutical dosage by the coordination of enzyme activity on a particular substrate material contained in the composition.

SUMMARY OF THE INVENTION

It is an object of this invention to provide a controlled release pharmaceutical composition.

It is a further object of the present invention to provide a controlled release pharmaceutical composition which reduces the frequency of drug administration while prolonging the level of pharmaceutical agents within a therapeutic range.

It is another object of this invention to prevent gastric irritation and gastric erosion which results from long term administration of conventional drug dosages.

A still further object of the present invention to prevent toxicity in the subject which is due to too rapid absorption of certain medicaments.

Finally, it is an object of the present invention to provide a controlled release pharmaceutical composition which can be conveniently administered orally in a normally liquid formulation.

These and other objects are achieved by providing a controlled release pharmaceutical composition which includes a solution or suspension vehicle and a pharmaceutically active agent. The composition is administered to the body in a normally liquid formulation which thereafter forms a semi-solid or gel-like matrix in the environment of the stomach thereby effecting controlled release of the pharmaceutically active agent.

DETAILED DESCRIPTION OF THE INVENTION

Figure 1:
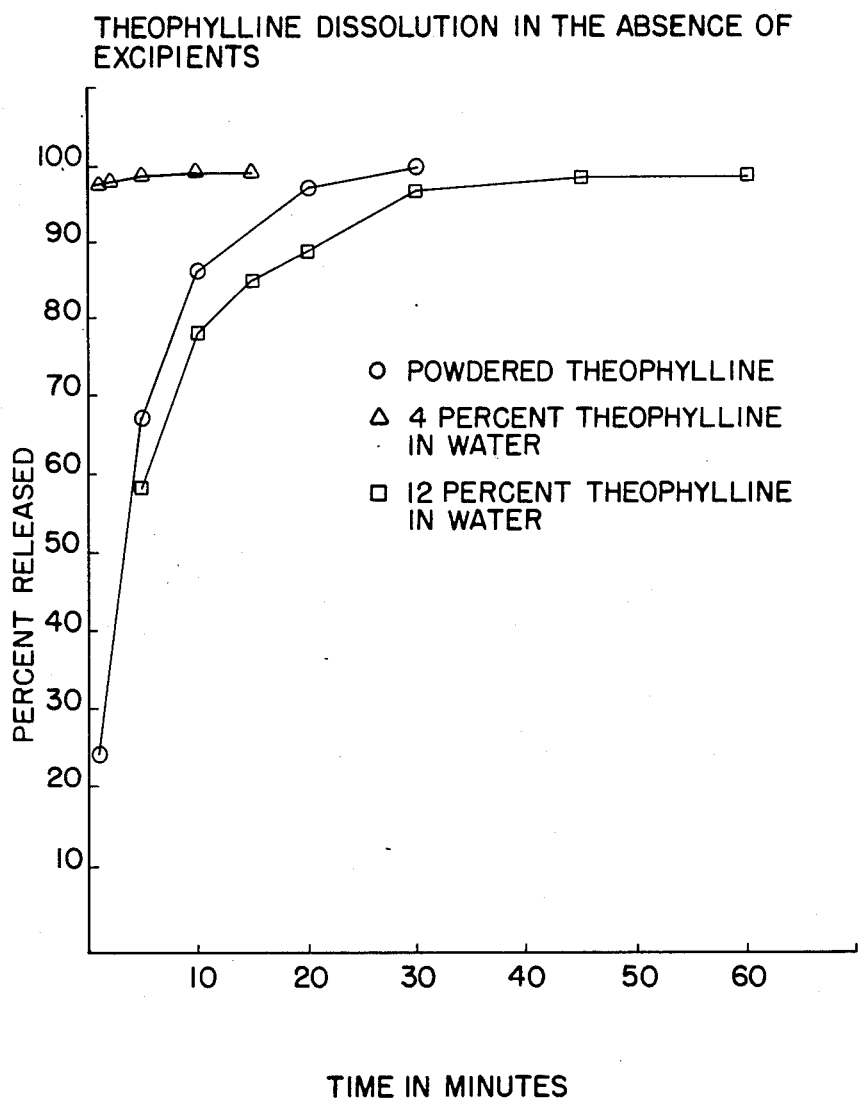
FIGS. 1-10 graphically depict the interval amount of theophylline (%) released into the dissolution medium as a result of in vitro testing of the controlled release systems of the present invention read at 272 nm (Spectrophotometer).
Figure 2:
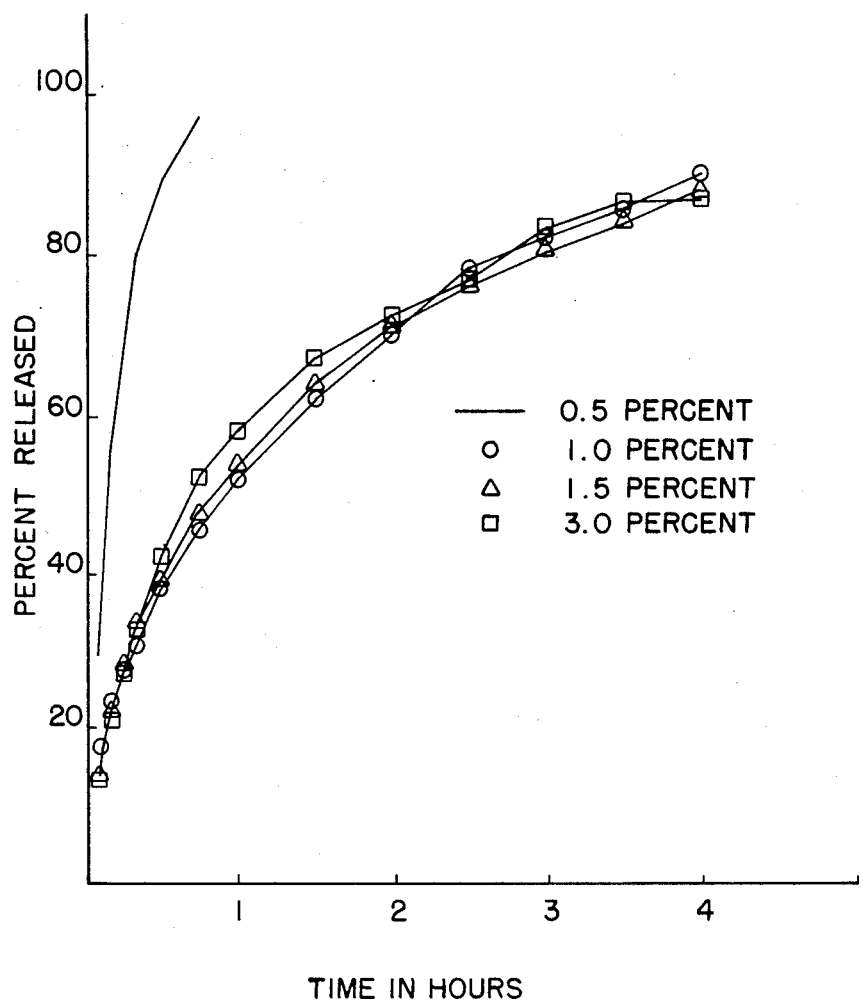
Figure 3:
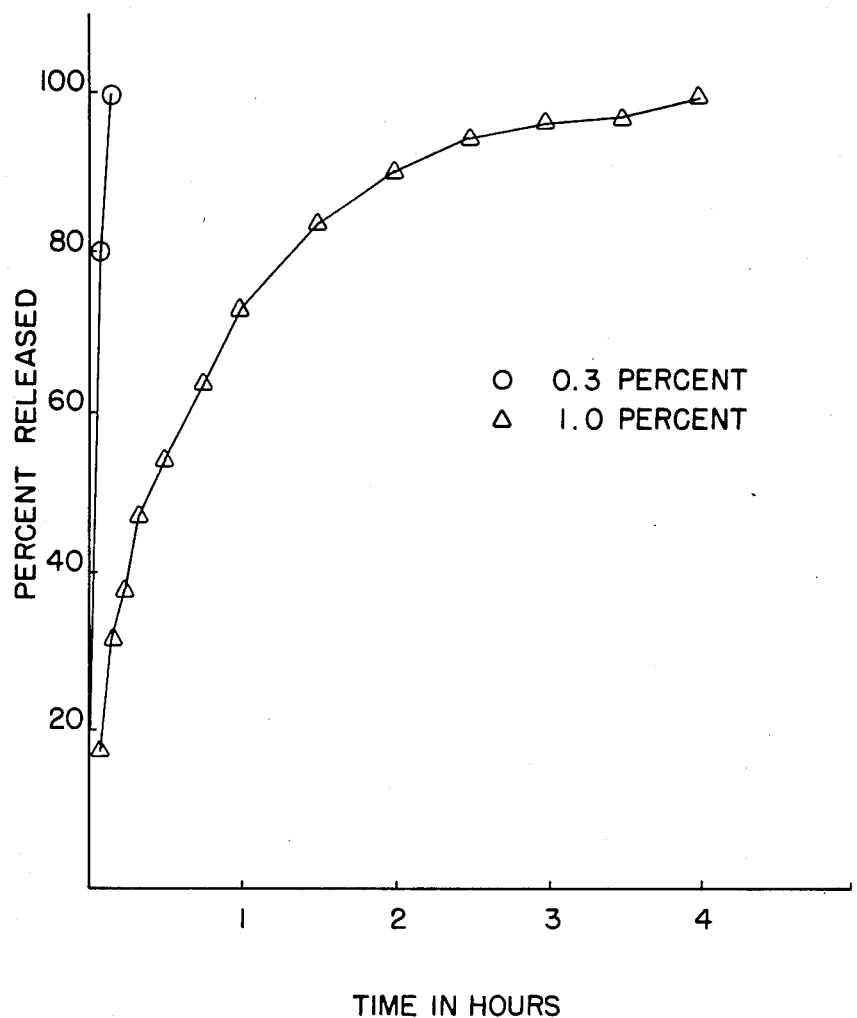
Figure 4:
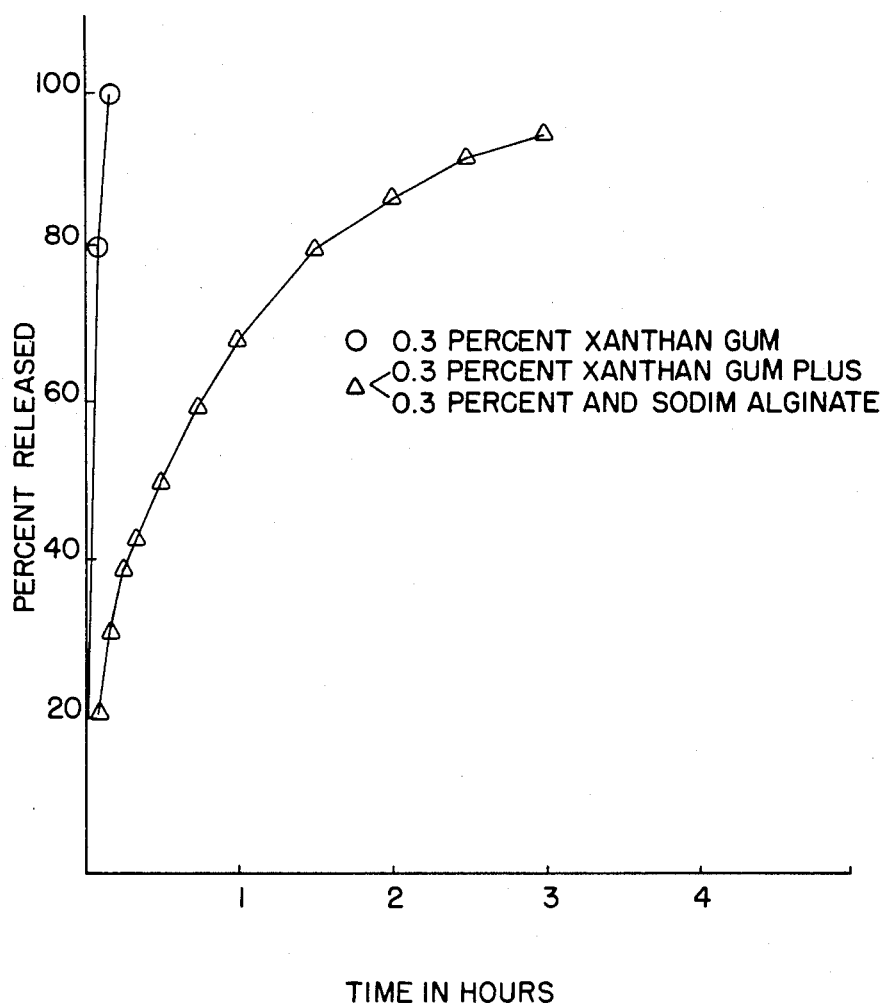
Figure 5:
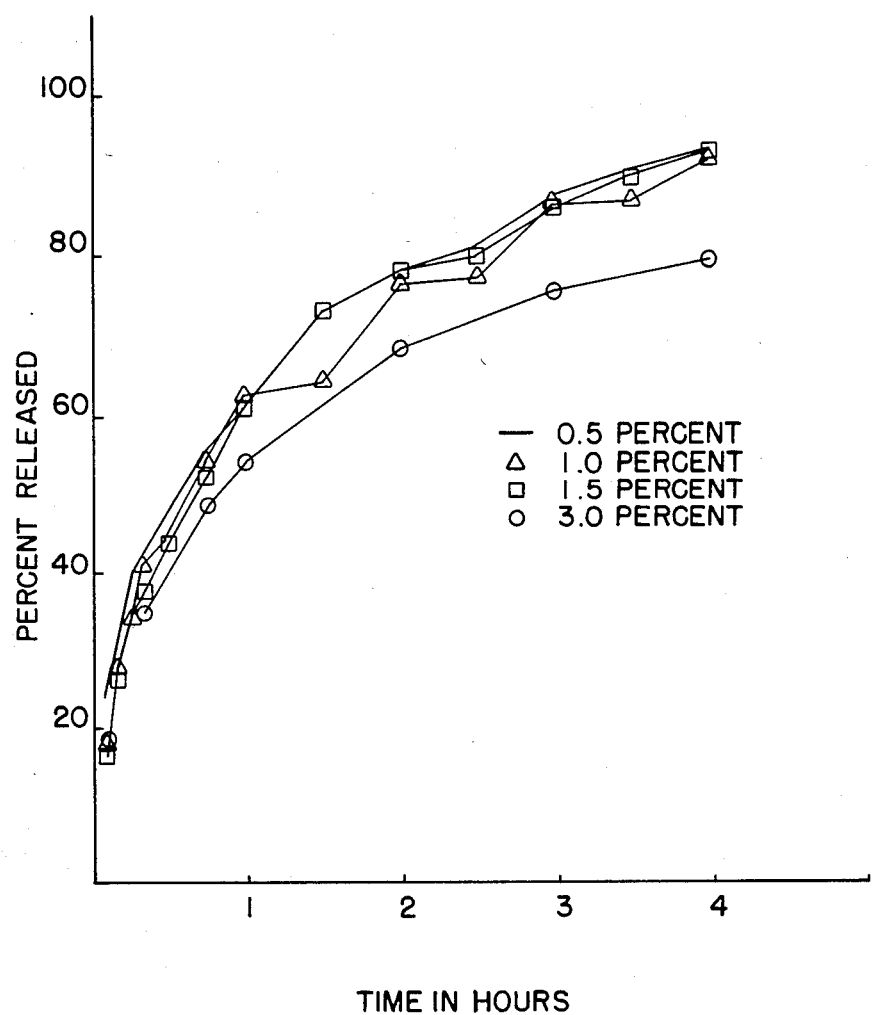
Figure 6:
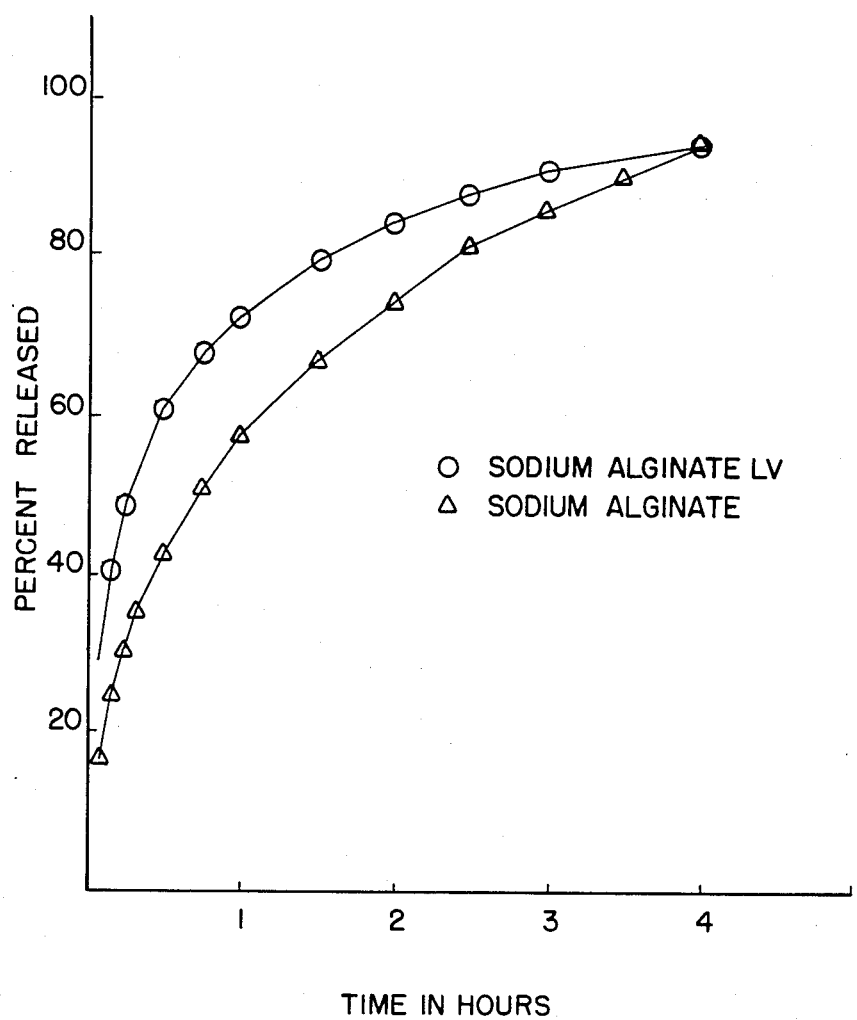
Figure 7:
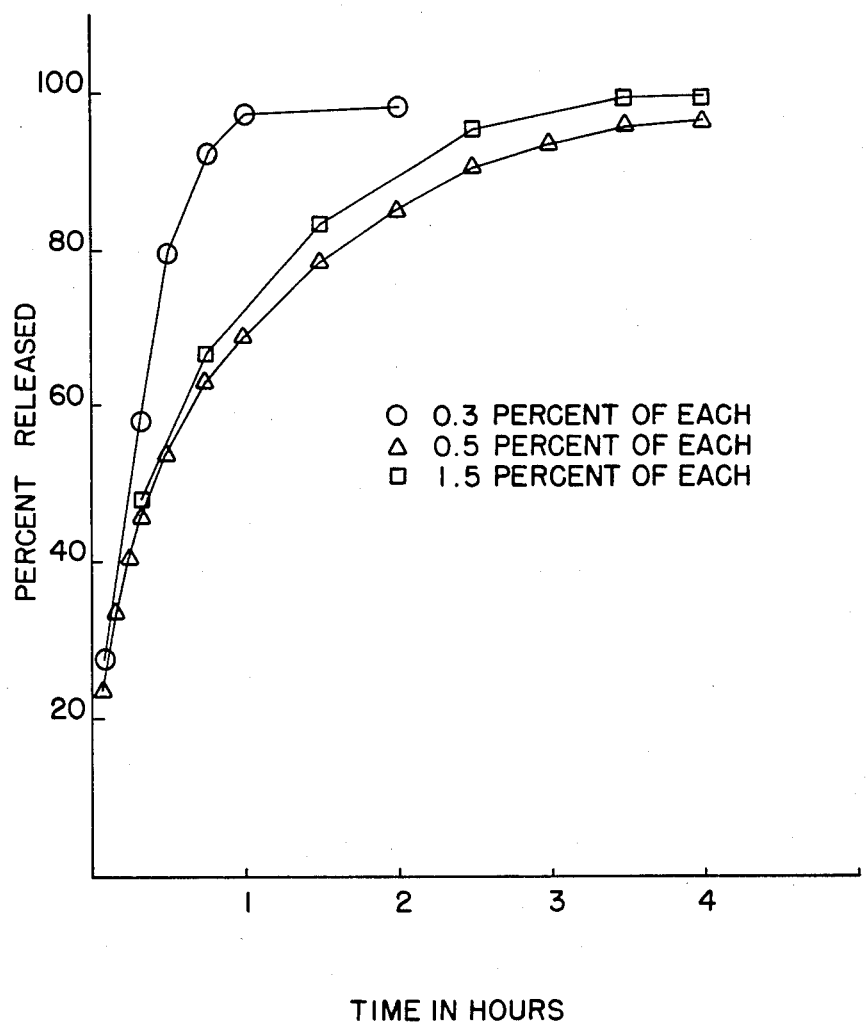
Figure 8:
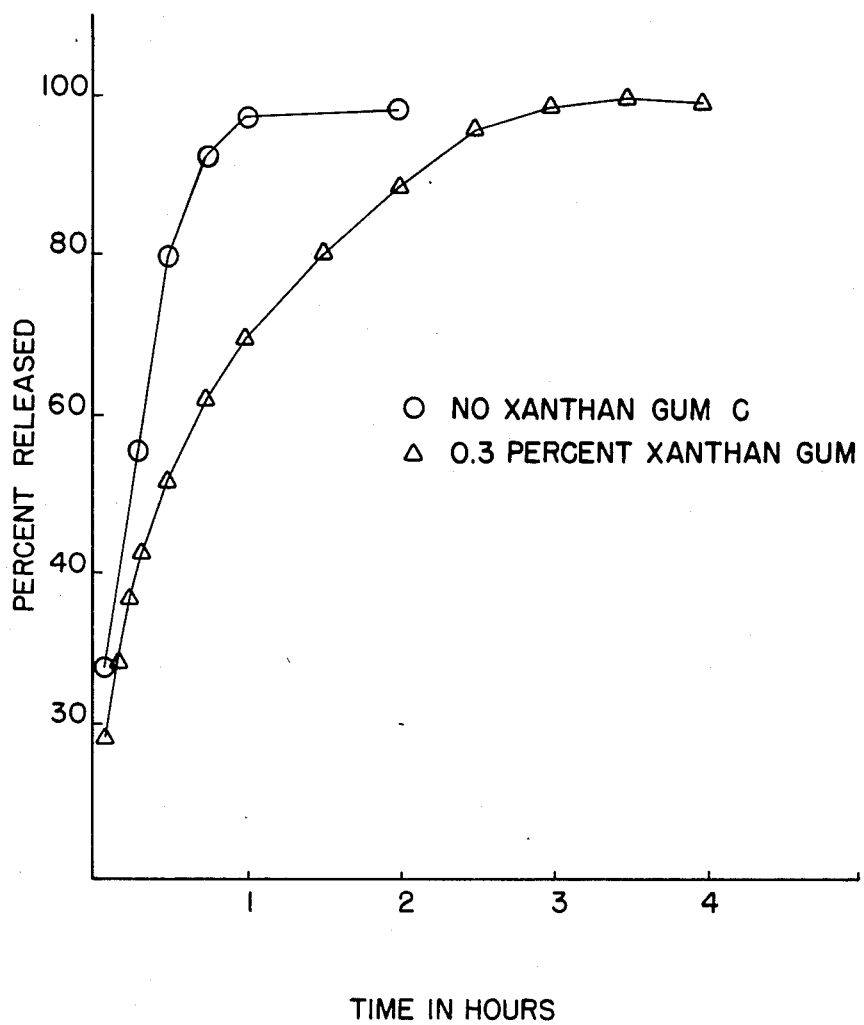
Figure 9:
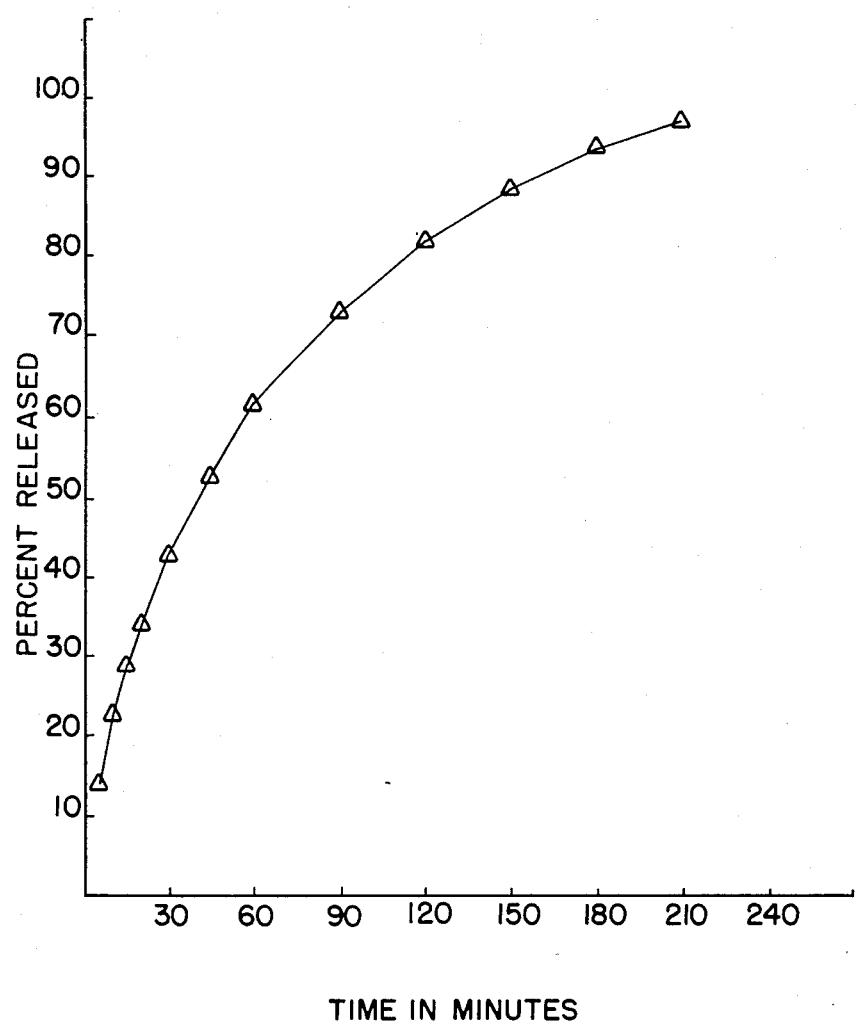
Figure 10:
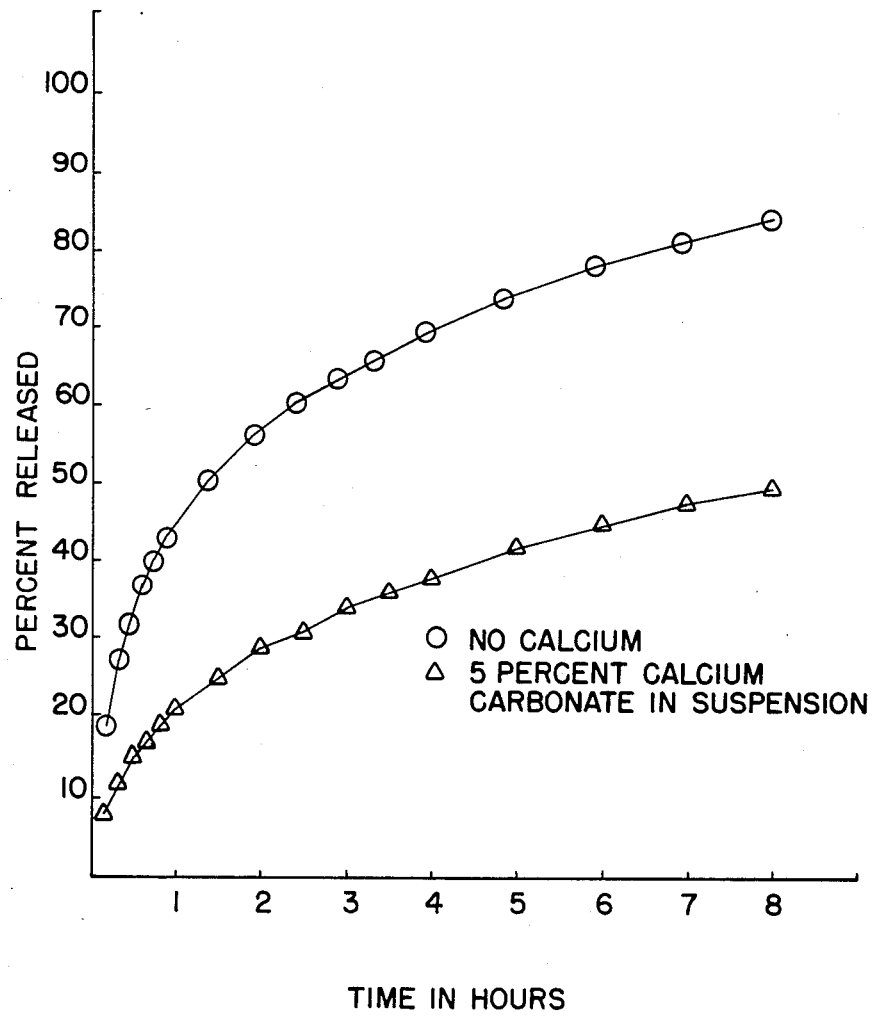
Figure 11:
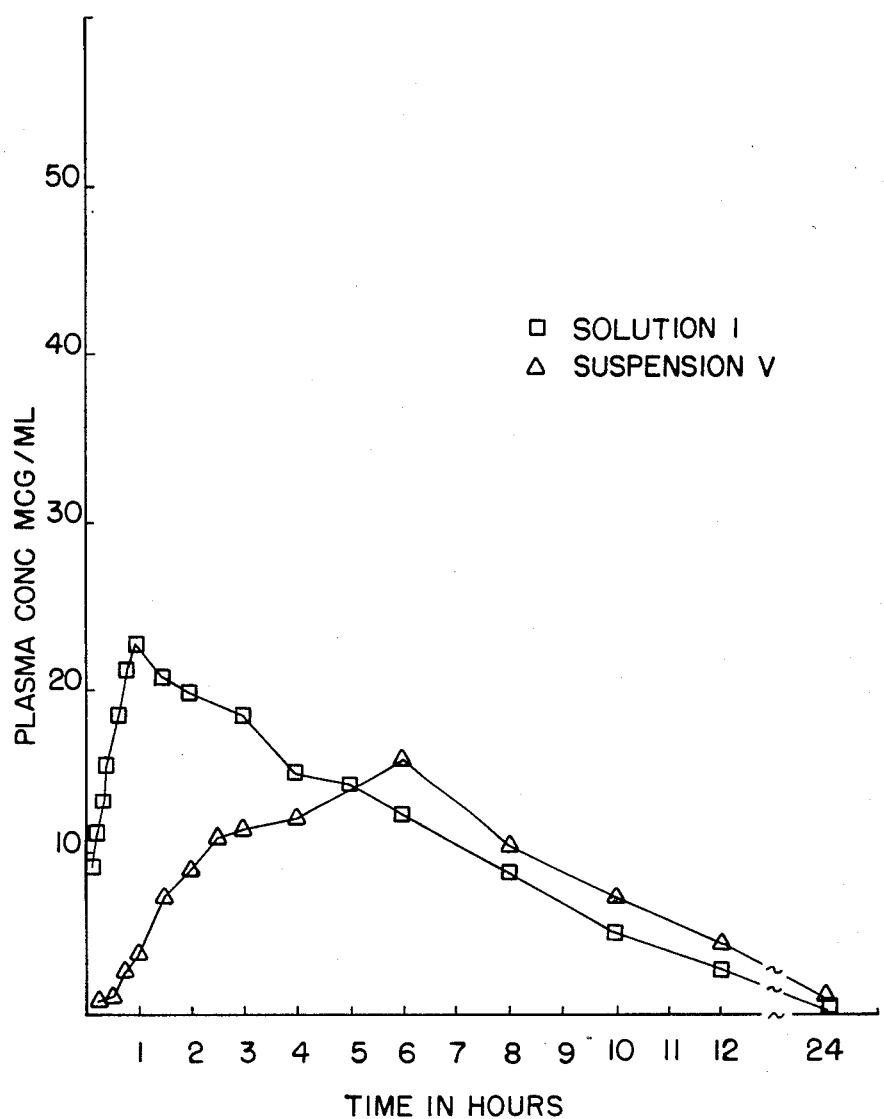
FIGS. 11-14 graphically depict the theophylline plasma levels ($\mu$g/ml) as a result of in vivo testing of the controlled release systems of the present invention read at 254 nm or at 280 nm (HPLC).
Figure 12:
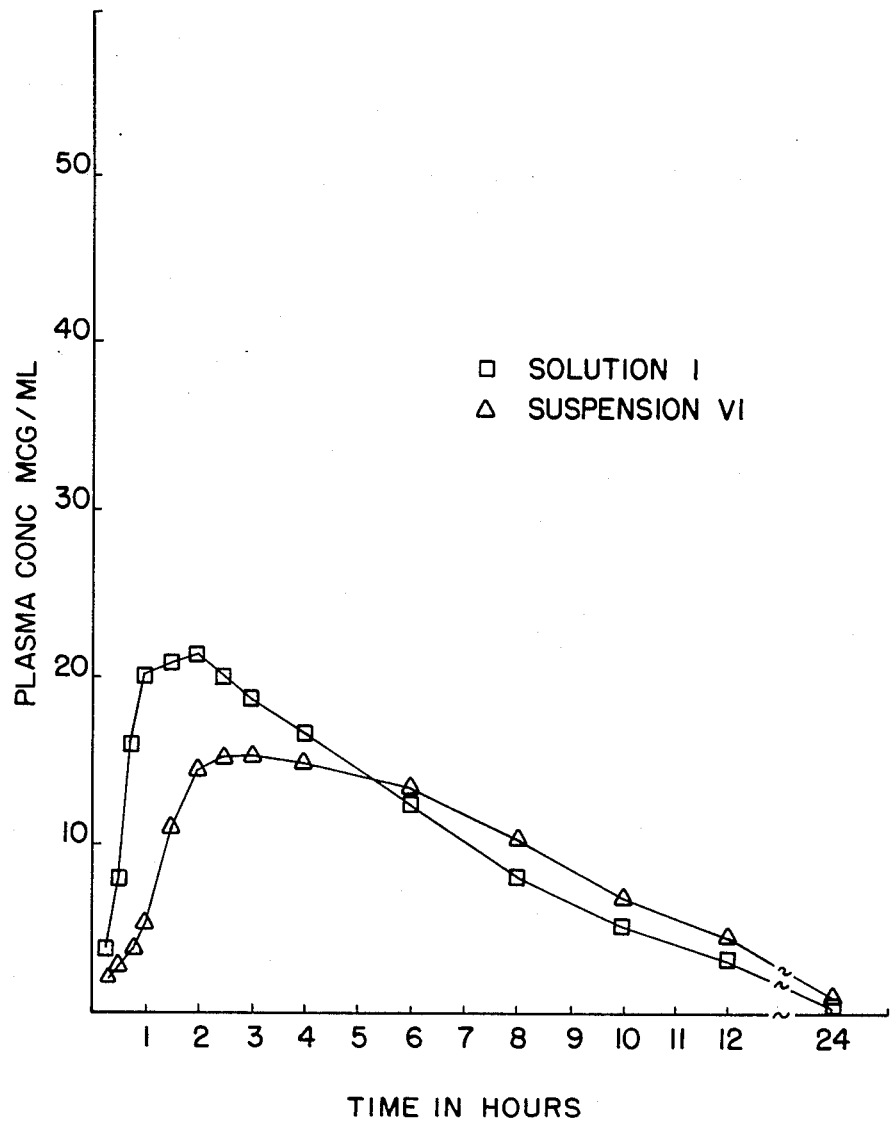
Figure 13:
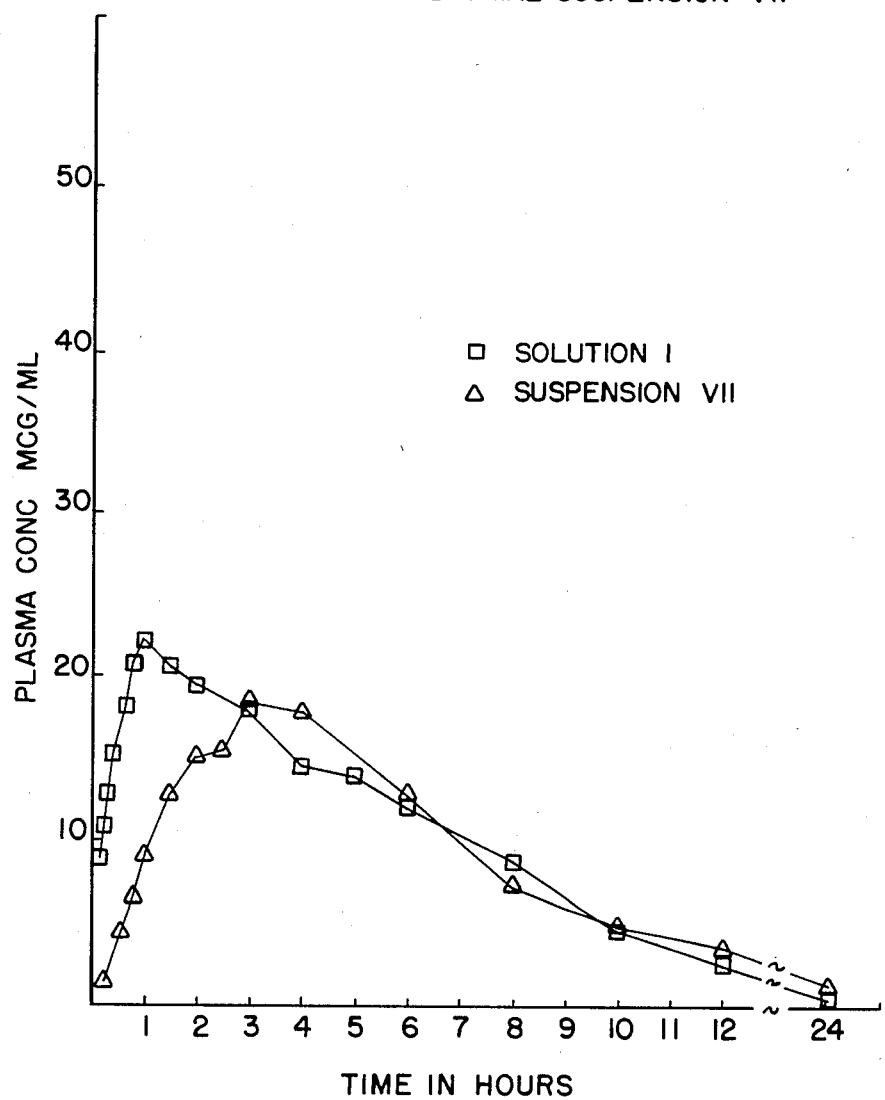
Figure 14:
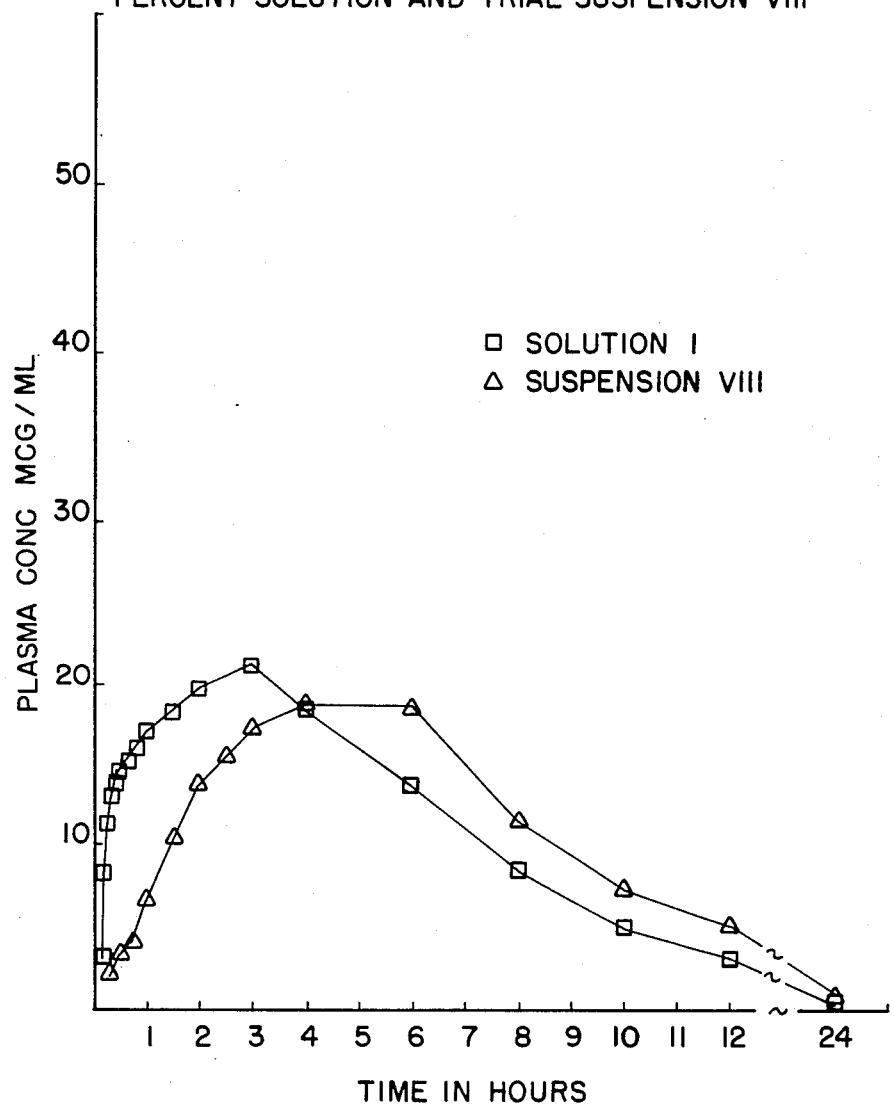

In accordance with the present invention, a pharmaceutical composition is provided which includes a solution or suspension vehicle and a pharmaceutically active agent. The composition is administered in a normally liquid formulation which thereafter forms a semi-solid or gel-like matrix in the environment of the stomach. The formation of this "bag of immobilized water" permits controlled release of the particular pharmaceutical agent employed.

The class of dosage forms known as suspensions and solutions provide a valuable adjunct in the treatment of a myriad of diseases. Moreover, the utilization of macromolecular excipients is known to influence drug dissolution and biological availability in several ways, e.g., by complexation with the particular drug, by increasing the bulk viscosity in the digestive tract or by delaying the disintegration of a suspension vehicle or the breakup of granules of drug into smaller particles or solid dosage forms.

In accordance with the present invention it has been surprisingly discovered that certain polymer compositions may be employed as vehicles for a wide array of medicaments, while exhibiting excellent controlled release characteristics. Furthermore, the present compositions may be conveniently administered in a normally liquid formulation thereby providing significant advantage in situations where the subjects, particularly young children and elderly patients, have difficulty swallowing tablets and/or capsules.

It has been further determined that these polymer solution or suspension vehicles are particularly effective due to the prompt formation of a rigid gelatinous matrix which results in the environment of the stomach after ingestion of the composition. The release is therefor controlled substantially by diffusion of the suspended drug through the matrix or molecules of the drug in solution which may have been first dissolved from particles of drug in suspension, although other factors such as surface tension, agitation, polymorphism effects, etc. may have some impact.

Generally, the present invention involves certain solution or suspension vehicles which include xanthan gum, sodium alginate, complex coacervate pairs such as gelatin or other polymers and carrageenan, and thermal gelling methycellulose formulations. Each have been found to influence the dissolution and/or diffusion rate of a suspended pharmaceutically active agent so as to favorably modify the absorption characteristics of the drug from a conventional dosage form. Advantageously, the compositions of the present invention may be administered in a normally liquid formulation and only subsequently form a semi-solid or gel-like persistent matrix in the environment of the stomach.

In more detail, the useful vehicles of this invention specifically include aqueous, partially aqueous or non-aqueous solutions or suspensions of xanthan gum, sodium alginate, or sodium alginate LV (low viscosity, calcium depleted), gelatin and carrageenan, methylcellulose and particular combinations thereof which are described below. Effective amounts of xanthan gum such as, for example, Kelco SS-4749 and other commercially available types, range from about 0.3 to about 3.0 percent by weight and preferably at least about 1.0 percent by weight. Excellent results were also obtained from compositions containing from about 0.5 to about 3.0 weight percent of sodium alginate or from about 0.3 to about 1.5 percent by weight of each gelatin and carrageenan. At least about 0.5 percent by weight of each carrageenan of the iota type and gelatin type B is preferred. Compositions containing at least about 1 weight percent of sodium alginate are also preferred. Methylcellulose (Type A15C, Dow Chemical Co.) was determined to be effective within a range of about 1.0 to about 3.0 weight percent and preferably about 2.0 weight percent.

It is also within the scope of the present invention to include certain amounts of other excipients such as, for example, locust bean gum, salts such as NaCl, sugars such as sorbitol, $Na_3PO_4$, $CaCO_3$, $Ca_2HPO_4$ and the like. Carbonate compounds such as calcium carbonate may be employed to "float" the gelatinous matrix in a predetermined region of the stomach so that it is contacted with the most appropriate pH environment for a prolonged time period due to delayed gastric emptying, which gas evolution technique is generally known, although the present method and choice of carbonate salt provides a formulation with excellent reproducibility for release of drug due to the controlled, gradual release of $CO_2$ gas. The preferred salt also exhibits a long term physical stability in excess of one year with respect to drug release characteristics.

The compositions of the present invention are to be administered in a liquid formulation which can include aqueous solutions or suspensions, partially aqueous solutions or suspensions such as, for example, high or low molecular weight glycerin, alcohols and glycols or even non-aqueous solutions or suspensions such as, for example, high or low molecular weight glycerin, alcohols and glycols.

Certain combinations of the aforementioned excipients have also evidenced significant controlled release efficacy. For example, combinations of sodium alginate or sodium alginate LV (Kelco-Gel LV) ranging from about 0.5 to about 1.5 weight percent with at least about 0.3 weight percent of xanthan gum or compositions containing at least 0.3 percent by weight of each carrageenan, gelatin and xanthan gum demonstrate good control release properties. The efficacy of the gelatin and carrageenan vehicle is improved by the addition of calcium carbonate. A composition containing about 2 weight percent of methylcellulose and about 5 weight percent sodium chloride is preferred as is the addition of about 5 weight percent of calcium carbonate to a suspension or solution of gelatin and carrageenan.

Inasmuch as the solution or suspension vehicles of the present invention provide a physical matrix which supports the incorporated pharmaceutical agent in a "bag of immobilized water", i.e., there is generally to chemical interaction significant to drug-release rate between the vehicle and the incorporated medicament, a myriad of pharmaceutical agents may be employed where treatment by way of controlled release administration of the drug is appropriate. It is apparent, therefore, that neither the pharmacologic nature of the active therapeutic ingredient nor the dosage in terms of concentration, to be incorporated into the controlled release composition of the instant pharmaceutical formulations are critical to the present invention. Examples of pharmaceutically active agents which may be employed in the present invention include analgesics and antiphlogistics such as aspirin, acetaminophen, phenacetin; steroids including antiflammatory steroids; enzymes, proteins, antibiotics or antimycrophotics including penicillin and its derivatives; anesthetics, vasodiolators such as nitroglycerin; narcotic antagonists, vitamins, anticarcinogins, sulfonamide drugs, sedatives, tranquilizing and hypnotic agents, bronchial-dilating agents, KCl and the like. Other medicaments requiring frequently repeated dosage by the oral route in order to maintain a therapeutically active blood level are particularly suitable for inclusion into the present controlled and prolonged release composition.

Thus, the scope and utility of the present controlled release compositions are not limited to any particular active ingredient. Furthermore, the controlled release mechanism and efficacy thereof is not limited to any category of active therapeutic compound but are a function of the properties of the new pharmaceutical composition formed.

In an effort to illustrate the controlled release properties of the present compositions, a common pharmaceutical agent which exhibits critical disadvantages when administered by conventional means was sought. By way of example, theophylline was selected since it is recognized as being one of the most frequently prescribed oral drugs useful in the treatment of asthma. The convenience of an oral formulation is heightened by statistics which evidence a broadly afflicted population which includes children and elderly patients who have difficulty swallowing tablets and capsules. Moreover, theophylline is rapidly absorbed into the body after oral dosages in liquid form and has a particularly short half-life necessitating frequent dosing. Lower levels are often ineffective whereas high levels often produce toxic symptoms ranging from headache, nausea and insomnia to cardiac arrythmias and seizures. Theophylline has also occasionally been found to act as a local gastric irritant. Theophylline is thus one drug which, by way of example, demonstrates a need to be administered so as to eliminate sharp blood peak levels and thereby avoid the disadvantages or conventional dosages.

Therefore, for a better understanding of the present invention together with other and further objects, reference is made to the following descriptions and examples.

EXAMPLES

In Vitro

Preparation of Solutions and Suspensions

Theophylline solutions were made by adding anhydrous theophylline powder to a weighed quantity of distilled water at room temperature containing 0.25 percent w/w of chlorobutanol preservative. The mixture was made in a tared screw-capped glass jar with a plastic cap and wax coated cardboard cap liner. After manual shaking, the mixture was stored at four degrees Centigrade until use. All formulas were made on a weight in weight basis.

Theophylline suspensions that did not contain gelatin and carrageenan were made by adding weighed theophylline anhydrous powder to a tared glass jar containing the required weight of distilled water preserved with 0.25 percent w/w chlorobutanol and shaking to slurry the theophylline. Next, weighed excipient powders were added to the mixture. All excipients were used as received. During addition of excipient powders, the mixture was agitated by a counter-rotating mixer. Agitation was continued until a fine dispersion was formed, the caps were screwed on and the jar stored at four degrees Centigrade overnight or longer until use. The refrigeration reduced the chance of spoilage and also assured complete hydration of excipients due to increased excipient solubility at low temperatures in some cases.

For suspensions containing calcium carbonate, the calcium carbonate powder was combined with theophylline powder prior to the addition of water to make a slurry. For theophylline suspensions containing gelatin and carrageenan, anhydrous therophylline powder was slurried in preserved water, then powdered carrageenan was slowly added and dispersed using a counter-rotating mixer. The required weight of gelatin was added to preserved water and heated to 75°–85° C. using another mixer until a clear solution was formed, then cooled to 50° C. The gelatin and carrageenan mixtures were then combined and dispersed using a mixer alternating with hand shaking. The mixer produced moderately high shear in a small region, whereas the manual shaking produced bulk mixing by a uniform low shear throughout the screw-capped glass jar. For gelatin/carrageenan suspensions containing calcium carbonate, the calcium carbonate powder was combined with the theophylline powder prior to the addition of water to make a slurry at room temperature. The slurry was stirred continuously so that a cake could not form. Next, gelatin and carrageenan powders were sifted into the vortex of the remaining water required at 95° C. using a counter-rotating mixer. When a clear solution was obtained, the aqueous slurry of theophylline and calcium carbonate was poured into the vortex of the stirred, 95° C. gelatin/carrageenan solution. Mixing was continued by alternating manual shaking with the mixer. It was necessary to put the suspension through a hand homogenizer to break up lumps that had formed. The final suspension was stored at four degrees Centigrade.

The suspensions containing dicalcium phosphate were made by adding 0.25 percent w/w of dicalcium phosphate powder to some of the theophylline suspension that had been made previously. The powder was dispersed by alternating manual shaking and machine mixing.

Diffusion Cell Studies

Experiments were performed to determine the possible effects of excipient addition on the release of theophylline from aqueous solution and suspension. Excipients used were: xanthan gum, sodium alginate, carrageenan and gelatin. The effect of theophylline concentration on release rate was also studied for certain excipient combinations discussed above. The diffusion data were used to confirm the release model and to identify factors controlling drug release from gelled systems.

In the diffusion cell study, the lower receptor compartments for two diffusion cells were used to form a single horizontal cell. A magnetic stirrer was mounted at a 90° angle and magnetic micro-bars were used, which rotated in the vertical plane against the receptor chamber bottom due to their slight weight.

A 1.2 micron filter membrane separated the donor compartment (containing non-stirred suspension) from the stirred receptor compartment.

A glass precision pipetter was used to re-fill the receptor chamber with 10 ml of simulated gastric fluid U.S.P. sans enzyme using a catheter. At each sample time, a 10 ml syringe was used to remove all receptor fluid via a catheter. Suspensions were warmed to 37° C. and centrifuged at $255 \times g$ (gravity) for 10 minutes, then manually stirred to assume homogeneity. Next, suspensions were loaded by a 20 ml syringe through a short piece of overfitting tubing via the "donor" diffusion cell access arm port. The suspension was bubble-free, having been made so by centrifuging at $255 \times g$. Frequent receptor fluid replacement maintained a sink receptor compartment due to very low receptor theophylline concentrations. The suspension was always incubated for 15 minutes at 37° C. for 15 minutes prior to use.

After two or three hours of release study progress, the donor cell was disassembled, and its suspension contents pushed out by low air pressure to allow measurement of the gelled region and depletion zone thicknesses, and to inspect the depletion zone for the presence of bubbles.

Dissolution Studies

Standard U.S.P. Teflon coated stainless steel paddles and round bottom glass beakers were employed. The desired stirrer speed was maintained by commercial feedback control circuitry (50 RPM is illustrated by way of example). The dissolution medium was 1000 ml of Simulated Gastric Fluid U.S.P. without enzyme in most cases, kept at 37° C. by a water bath with a heat/circulator unit.

Suspension was placed into the filled beaker near the surface by 0.27 cm inner radius glass tube attached by plastic tubing to a three ml disposable syringe. Two ml of suspension was pulled up into the tube, the exterior wiped clean, one ml was extruded into the dissolution medium beneath the surface, and the suspension separated from the glass tube by cutting with a razor blade. The technique produced uniform cylindrical matrices in most cases. The highest drug concentration used was 120 mg/ml, so that the concentration of drug in the beaker never exceeded 1.1 percent of solubility, a sink condition.

Dissolution Study Sample Analysis

In all cases, the total amount of drug released into the dissolution medium was less than ten percent of that needed to saturate the medium, so that sink conditions were maintained.

A precise volume was withdrawn near the top of the dissolution medium for each sample. The volume ranged from 0.1 ml to 3.0 ml. In some cases, sample volumes were replaced with fresh dissolution medium.

Standard curves were concentrated for theophylline in simulated gastric fluid USP. Samples were diluted to read within the linear concentration range and absorbance was read at 272 nm using a single beam spectrophotometer.

Theophylline Solubility Determination

Anhydrous theophylline was used to make a standard solution of 10 micrograms/ml in distilled water.

Excess theophylline was placed in test tubes with either distilled water or simulated gastric fluid USP without enzyme. These suspensions were kept overnight at 37° C. Three ml disposable syringes and filter holders with cellulosic filters were kept at 37° C. also. Small Teflon coated magnetic stirbars maintained agitation overnight. Each mixture was filtered, an aliquot of filtrate was diluted with distilled water, and theophylline absorbance was read at 272 nm and compared to that of the 10 μg/ml standard solution.

The results of the aforedescribed in vitro experimentation employing the various compositions of the present invention are set forth in the Tables I–X, below.

TABLE I

Dissolution of Theophylline At 50 R.P.M. From Suspension Containing 4% Theophylline and 96% Water After Delivery by Glass Tube

| Time Minutes | Percent Released |
|---|---|
| 1 | 97.56 |
| 2 | 97.91 |
| 5 | 98.79 |
| 10 | 99.14 |
| 15 | 99.13 |

TABLE II

Dissolution of Theophylline at 50 R.P.M. With No Polymers Present

| Excipients | Theophylline System and Amount | | T 50% (Minutes[1]) |
|---|---|---|---|
| None | Powder | 42 mg | <5 |
| chlorobutanol | 4% Suspension | 1 ml | <1 |

[1]Time for 50% theophylline to dissolve.

TABLE III

The Effect of Concentration of Xanthan Gum at 50 RPM for 50% Dissolution of 4% Theophylline From Suspension

| Xanthan Gum Concentration | T 50% (Minutes) |
|---|---|
| 0.5% | 10 |
| 1.0% | 50 |
| 1.5% | 41 |
| 3.0% | 56 |

TABLE IV

The Effect of Added Locust Bean Gum or Added Sodium Alginate on the Time for 50% Dissolution of 4% Theophylline From Xanthan Gum Suspensions at 50 R.P.M.

| Excipients and Concentration | | T 50% (Minutes) |
|---|---|---|
| Xanthan Gum[1] | 0.3% | 5 |
| Xanthan Gum | 1.0% | 25 |
| Xanthan Gum and | 0.3% | 10 |
| Locust Bean Gum | 0.3% | |
| Xanthan Gum and | 0.3% | 30 |
| Sodium Alginate | 0.3% | |

[1]Xanthan Gum, Very Chunky Flow, high viscosity type.

TABLE V

The Effect of Sodium Alginate Concentration on the Time for 50% Dissolution of 4% Theophylline From Suspension at 50 R.P.M.

| Sodium Alginate Concentration | T 50% (Minutes) |
|---|---|
| 0.5% | 31 |
| 1.0% | 39 |
| 1.5% | 40 |
| 3.0% | 45 |

TABLE VI

Effect of Polymer Concentration on Dissolution of 4% Theophylline from Suspensions Containing Equal Concentrations of Gelatin and Carrageenan at 50 R.P.M.

| Concentration of Each Polymer | T 50% (Minutes) |
|---|---|
| 0.3% | 15 |
| 0.5% | 25 |
| 1.5% | 22 |

TABLE VII

Effect of Added Xanthan Gum on the Time for 50% Dissolution of 4% Theophylline from Suspensions Containing 0.3% Gelatin and 0.3% Carrageenan

| Additional Excipient | T 50% (Minutes) |
|---|---|
| none | 15 |
| 0.3% Xanthan Gum (Kelco SS-4749) | 28 |

TABLE VIII

Dissolution of Theophylline at 50 R.P.M. From Suspensions Containing 4% Theophylline, 2% Methylcellulose and 5% Sodium Chloride After Delivery by Glass Tube

| Time Minutes | PERCENT RELEASED | | | | |
|---|---|---|---|---|---|
| | A | B | C | Mean | Std. Dev. |
| 5 | 15.06 | 14.24 | 13.32 | 14.21 | 0.87 |
| 10 | 24.09 | 22.19 | 22.19 | 22.82 | 1.10 |
| 15 | 29.35 | 29.68 | 28.09 | 29.04 | 0.84 |
| 20 | 34.60 | 35.17 | 33.25 | 34.34 | 0.99 |
| 30 | 43.00 | 44.16 | 42.09 | 43.08 | 1.04 |
| 45 | 53.18 | 53.30 | 52.09 | 52.85 | 0.67 |
| 60 | 61.25 | 62.57 | 61.20 | 61.67 | 0.78 |
| 90 | 72.16 | 75.02 | 72.20 | 73.13 | 1.64 |
| 120 | 81.11 | 83.82 | 81.00 | 81.97 | 1.60 |
| 150 | 87.66 | 89.87 | 88.32 | 88.62 | 1.13 |
| 180 | 92.87 | 94.41 | 94.31 | 93.86 | 0.86 |
| 210 | 95.99 | 98.79 | 97.38 | 97.39 | 1.40 |

TABLE IX

The Effects of Calcium Addition to the Dissolution Medium and Calcium Addition to Suspensions on the Time for 50% Theophylline Dissolution from 4 Percent Theophylline Suspensions Containing Sodium Alginate, and Sodium Alginate Plus Xanthan Gum at 50 R.P.M.

| Excipient Concentration | Calcium Concentration | T 50% (Minutes) |
|---|---|---|
| Sodium Alginate 0.5% | zero | 31 |
| | 5 meq/l beaker | 32 |
| Sodium Alginate 1.0% and Xanthan Gum (Kelco SS-4749) 0.3% | zero | 46 |
| | 0.25% $Ca_2HPO_4$ in suspension | 39 |
| Sodium Alginate LV 1.0% and Xanthan Gum (Kelco SS-4749) 0.3% | zero | 17 |
| | 0.25% $Ca_2HPO_4$ in suspension | 30 |

TABLE X

The Effect of 5 Percent Calcium Addition on the Dissolution of 12 Percent Theophylline Suspension Containing 0.5% Each Gelatin and Carrageenan at 50 R.P.M.

| Calcium Concentration | T 50% (Hours) |
|---|---|
| zero | <2 |
| 5% Calcium Carbonate in suspension | >7 |

EXAMPLES

In Vivo

Suspension and Solution Manufacture for Gastric Intubation Studies

For theophylline solutions, anhydrous theophylline powder, one percent w/w, was added to distilled water and manually shaken in a screw-capped glass jar, then kept at four degrees Centigrade until used.

For most theophylline suspensions, the required weight of powdered drug was added to distilled water in a screw-capped jar, then the excipient powder was added to the theophylline slurry while stirring with a counter-rotating mixer until a coarse dispersion was made. Next the suspension was shaken by hand, then kept at four degrees Centigrade overnight until used. This prevented spoilage and also allowed hydration of excipients. All suspensions were preserved with 0.25 percent w/w/ chlorobutanol.

Before administration to dogs, the solutions and suspensions were warmed to room temperature with occasional hand stirring using a glass rod. After use, all mixtures were again stored at four degrees Centigrade.

For the gastric intubation study using a gelatin/carrageenan formula a three percent w/w gelatin solution was made at 75° C., then cooled to room temperature. Theophylline powder was slurried in water, in which carrageenan powder was next dispersed using a counter-rotating mixer. Lastly, the gelatin solution and theophylline and carrageenan slurry were combined in a screw-capped glass jar using hand shaking and a counter-rotating mixer alternatively. Hydration of polymers was completed by overnight refrigeration at four degrees Centigrade.

Suspension Manufacture for Capsule Delivery Studies

For gelatin/carrageenan suspensions containing calcium carbonate, the calcium carbonate powder was combined with the theophylline powder prior to the addition of water to make a slurry at room temperature. The slurry was stirred continuously so that a cake could not form. Next, gelatin and carrageenan powders were sifted into the vortex of the remaining water required at 95° C. using a counter-rotating mixer. When a clear solution was obtained, the room temperature aqueous slurry of theophylline and calcium carbonate was poured into the vortex of the stirred, 95° C. gelatin/carrageenan solution. Mixing was continuous by alternating manual shaking with use of the mixer. It was necessary to put the suspension through a hand homogenizer to break up lumps that had formed. The final suspension was stored at four degrees Centigrade.

The suspensions containing dicalcium phosphate were made by adding 0.25 percent w/w of dicalcium phosphate powder to some of the theophylline suspension that had been made previously. The powder was dispersed by alternating manual shaking and machine mixing.

Study Protocol for Gastric Intubation Studies

One dosage form was studied for a one week time period. The dog to be used on a particular weekday was randomly selected so that three dogs were studied on three days during the week. A minimum washout period of five days was observed between different formulations.

On the evening before the study day, the chosen dog was fasted after six p.m. The fast continued until six hours after dosing on the next day, which was the study day. No water was allowed from one hour before until six hours after dosing on the study day. The six hour meal was 180 g of commercial regular dog chow, yielding approximately 675 calories. Water was allowed ad libidum beginning six hours after dosing.

On the study day, both forelegs were shaved over the cephalic vein area, then swabbed with 70 percent isopropanol. Next 22 gauge one inch teflon catheter was placed bevel up atop the vein. The needle was raised to a 30° angle and the point quickly pressed a small distance into the vein, which was compressed. At this point, needle pressure was removed and reapplied in stages to puncture the proximal vein wall, yet not the distal vein wall, as the vein was nearly collapsed. Correct placement of the needle was indicated by blood flow out to the end of the catheter filter. Once the needle was correctly positioned, the needle and catheter sheath assembly/skin angle was reduced to align the needle with the center axis of the vein, and the needle/catheter sheath assembly was pushed up the vein until the catheter was fully inserted. Next, an injection cap was prepared, and needle and catheter filter was removed, leaving the catheter and hub inside the vein. A few drops of blood were permitted to fall from the open catheter hub indicating correct insertion and an open line, then the injection cap was twisted onto the hub. The catheter head was lightly secured with one inch porous cloth adhesive tape so as not to put pressure on the caphalic vein. Immediately after installation, one ml of normal saline with 10 units/ml heparin was injected into the injection cap.

Once catheter installation was finished, the dog's jaws were opened and a roll of one inch adhesive tape was placed in the mouth and the jaws held closed on the tape roll using one hand. Using the other hand, a clear 11 mm outer diameter/6.5 mm inner diameter piece of plastic tubing was wetted in water and quickly pushed through the open center of the tape roll and into the dog's throat using light pressure. When the dog swallowed the tube was advanced until a black mark on the tube, obtained by measurement of the distance from the nose to the zyphoid process in normal posture, was even when the dog's nose. Next the free tube end was placed in a beaker of water to check for the absence of bubbling, which would indicate that the tube had been inserted into the bronchial tree. Following this, three ml of water was squirted into the tube for a second insertion location check. Coughing would dictate reinsertion of the gastric tube.

The tube end was then clamped in place and the dosing syringe was attached by friction fit. The 50 ml plastic syringe contained a weight of suspension equal to the weight required to fill the gastric tube plus the dose. The syringe was emptied and the tube removed from the dog. the tube exterior was then wiped dry and weighed to determine the actual weight of suspension delivered. The target dose was 30 mg/kg. For administration of solutions only, a smaller opaque butyl rubber gastric tube was used and the dose was followed by 20 ml of distilled water.

Three ml of blood was withdrawn at the following times: −5 (blank), 5, 10, 15, 20, 25, 30, 40 and 50 minutes and 1.0, 1.5, 2.0, 3.0, 4.0, 5.0, 6.0, 8.0, 10, 12 and 24 hours. Three ml 21 gauge disposable syringes were used. Before blood was drawn 0.2 ml was taken from the injection cap to remove the heparinized normal saline flush, as the catheter and cap volume was 0.1 ml. Immediately after blood was taken, one ml of heparinized saline flush was injected.

After two hours in the harness, a chrome plated wire-ended muzzle secured by leather strap was placed on the dogs and they were removed from the harness and allowed to exercise. After six hours the dogs were placed in cages and allowed access to food and water. The muzzle prevented the dogs from chewing and pulling out the catheter, and was oversized so that eating and drinking was possible.

Some dogs become troublesome at the end of the gastric intubation studies. The dogs began to learn ways to bite out the catheters despite the presence of muzzles. Direct venipuncture became necessary, and the use of catheters was abandoned.

Study Protocol for Suspensions Delivered in Capsules

The time sequence of dog studies was begun by random assignment of two dogs to the first capsule study date. The remaining two dogs, by default, were therefore assigned to the following day.

The formulation to be used for the first dog and first study date was randomly chosen, so that by default, an alternate formulation was used on the second dog and the first date. By default, the dogs were crossed over to alternate formulations on the following study date.

Later in the series of experiments, the pattern of studies was disrupted when some dogs crushed the capsules during dose administration. This necessitated rescheduling the dog for a later date using the same formulation.

For capsule studies, dogs were fed at six p.m. on the night prior to the study day, then fasted until six hours after dosing. Water was not allowed from one hour before to six hours after dosing. The fast was 18 hours at minimum, occasionally longer due to problems in obtaining cooperation from the dogs. The six hour meal was 180 grams of regular commercial dog chow.

On the study day, both forelimbs were shaved over the cephalic vein area and swabbed with 70 percent isopropranol, which served to disinfect, render the fur translucent to help visualize the vein, and also to engorge the vein with blood. Using a firm grip above the elbow, yet not so tight as to reduce arterial blood flow into the limb, the paw was rhythmically squeezed to pump blood up into the vein. Next a 21 gauge one inch needle with attached three ml disposable plastic syringe attached was placed bevel up atop the vein. The needle was raised to a 30° angle and the point quickly pressed a small distance into the vein, which was compressed. At this point, needle pressure was removed and reapplied in stages to puncture the proximal vein wall, yet not the distal vein wall, as the vein was nearly collapsed. During this process, the 4th and 5th fingers were used to pull the plunger, so that blood would flow freely into the syringe immediately upon correct positioning of the needle. Once the needle tip was correctly positioned, the needle/skin angle was reduced so that the needle was aligned with the central axis of the vein and the needle was pushed upward into the vein so that one cm was inserted. Then blood was drawn up with no pressure above the elbow, except on the bony joint areas, to allow faster filling of blood into the syringe. Minimal pull on the plunger prevented collapse of the vein by too rapid a withdrawal of blood. The needle was then withdrawn and firm pressure applied to the puncture site for 0.5 to 1.0 minute to allow clotting of blood at the puncture site, to prevent bleeding. Punctures were started as high as possible in the cephalic vein so that an entire study was done utilizing one vein, and the alternate leg vein was used for the subsequent study. This allowed the veins to heal between studies.

Samples were withdrawn at the following times: −5 (blank), 15, 30, 45 minutes and 1.0, 1.5, 2.0, 2.5, 3.0, 4.0, 6.0, 8.0, 10, 12 and 24 hours.

Preparation of Blood Samples

After each sample was obtained, the syringe needle was removed and then the blood was expressed into a 13 mm×100 mm screw-capped glass test tube containing 30 units of dried sodium heparin. Teflon coated caps were screwed on the test tube, and the tube rocked gently to dissolve and mix the heparin and blood. Blood samples were kept at four degrees Centigrade until centrifugation at 1500 rpm for 30 minutes to separate the plasma, which was either used immediately or frozen until later use.

One ml of plasma was transferred to a clean 13 mm×100 ml glass test tube, 100 microliters of 480 micrograms/ml internal standard in pH 4.0 acetate buffer was added, then 100 microliters of 40 percent trichloroacetic acid in distilled water was added to precipitate proteins. The test tubes were then capped and centrifuged at 2000×g for 15 minutes. The supernatant was transferred to a clean 13 mm×100 mm test tube, capped and kept at four degrees Centigrade until analysis by high performance liquid chromatography. The remaining unused plasma was placed in a disposable 12 mm×75 mm flint glass test tube, sealed with a polyethylene plug, and frozen in case a repeat analysis proved necessary. Analysis was effected by High Performance Liquid Chromatography with detection at 254 nm using caffeine as an internal standard or detection at 280 nm using beta-hydroxyethyl theophylline as a standard.

It should be particularly noted that the capsules utilized in the experimental studies of the present invention were employed only for purposes of convenience and in an effort to obtain more accurate testing results since administration of the present compositions via gastric intubation was problematic, increasing the risk of vomiting and overall resistance on the part of the dogs. The capsules containing the liquid formulation of the aforementioned compositions had no significant effect on the time release properties studied but, merely provided convenience and complete administration of the present compositions to the dogs. For example, Table XII represents the significant differences in absorption times observed during the in vivo testing. Particular difficulty in administration by intubation using Formula II can be observed therein. Table XI defines the specific compositions tested.

The results of the aforedescribed in vivo experimentation employing the different compositions of the present invention are set forth in Tables XII–XXXIX below.

TABLE XI

Theophylline Formulations Tested In Vivo

| | Ingredients | Concentration | Delivery Mode |
|---|---|---|---|
| I | Theophylline | 1% | Gastric Tube |
| | Water | balance | |
| II | Theophylline | 4% | Gastric Tube |
| | Gelatin | 1.5% | |
| | Carrageenan | 1.5% | |
| III | Theophylline | 4% | Gastric Tube |
| | Sodium Alginate | 3% | |
| IV | Theophylline | 4% | Gastric Tube |
| | Xanthan Gum | 3% | |
| V | Theophylline | 12% | Capsule |
| | Sodium Alginate | 1% | |
| | Calcium Carbonate | 5% | |
| VI | Theophylline | 12% | Capsule |
| | Sodium Alginate | 1% | |
| | Xanthan Gum C | 0.3% | |
| VII | Theophylline | 12% | Capsule |
| | Gelatin | 0.5% | |
| | Carrageenan | 0.5% | |
| | Calcium Carbonate | 5% | |
| VIII | Theophylline | 12% | Capsule |
| | Xanthan Gum | 1.5% | |

TABLE XII

Summary of statistical comparison of in vivo absorption of theophylline from test suspensions compared to aqueous solution administered to same dog based on analysis of blood levels

| Test Formula | Absorption Times | | |
|---|---|---|---|
| | 25% | 50% | 75% |
| II | not significant | not significant | not significant |
| III | P < 0.20 | not significant | not significant |
| IV | P < 0.20 | P < 0.20 | P < 0.10 |
| V | P < 0.05 | P < 0.05 | P < 0.05 |
| VI | not significant | not significant | not significant |
| VII | P < 0.10 | P < 0.10 | P < 0.10 |
| VIII | P < 0.20 | not significant | P < 0.20 |

Not Significant - Indicates no statistically significant difference
P - Indicates significant statistical difference
P values - Indicate level of significance

TABLE XIII

Theophylline Plasma Concentrations, Area Under the Plasma Level/Time Curve and Percent Absorbed for Dog A After Administration of Formula I by Gastric Intubation

| Time Hours | Plasma Concentration MCG/ML | Cumulative* A.U.C. | Percent Absorbed** |
|---|---|---|---|
| 0.10 | 4.18 | 0.21 | 12.28 |
| 0.18 | 11.80 | 0.85 | 34.73 |
| 0.26 | 16.13 | 1.97 | 47.80 |
| 0.33 | 18.46 | 3.23 | 55.11 |
| 0.42 | 20.07 | 4.90 | 60.51 |
| 0.50 | 21.04 | 6.55 | 64.01 |
| 0.67 | 21.47 | 10.16 | 66.74 |
| 0.83 | 22.20 | 13.66 | 70.30 |
| 1.00 | 24.06 | 17.59 | 77.32 |
| 1.50 | 25.68 | 30.02 | 87.13 |
| 2.00 | 28.01 | 43.45 | 99.45 |
| 3.00 | 29.99 | 72.45 | 117.12 |
| 4.00 | 25.92 | 100.41 | 116.73 |
| 6.00 | 19.48 | 145.81 | 116.57 |
| 8.00 | 11.92 | 177.21 | 107.45 |
| 10.00 | 7.33 | 196.46 | 101.97 |
| 12.00 | 4.92 | 208.71 | 99.95 |
| 24.00 | 0.92 | 243.74 | 102.69 |

Elimination Constant = .1408 $HR^{-1}$
*For tables XIII through XXXIX calculation is based on area under blood-time curve from 0 to 24 hours based on the trapazoidal rule.
**Calculated by Wagner-Nelson method. (Tables XIII-XXXIX)

TABLE XIV

Theophylline Plasma Concentrations, Area Under the Plasma Level/Time Curve and Percent Absorbed for Dog B After Administration of Formula I by Gastric Intubation

| Time Hours | Plasma Concentration MCG/ML | Cumulative A.U.C. | Percent Absorbed |
|---|---|---|---|
| 0.08 | 16.73 | 0.67 | 42.75 |
| 0.17 | 33.39 | 2.92 | 86.04 |
| 0.25 | 37.55 | 5.96 | 97.88 |
| 0.33 | 37.47 | 8.76 | 99.03 |
| 0.50 | 35.52 | 14.97 | 96.83 |
| 0.67 | 37.90 | 21.21 | 105.68 |
| 0.83 | 32.22 | 26.82 | 93.76 |
| 1.00 | 34.71 | 32.50 | 102.63 |
| 1.50 | 32.59 | 49.33 | 104.78 |
| 2.00 | 30.10 | 65.00 | 105.49 |
| 3.00 | 26.11 | 93.11 | 107.93 |
| 4.00 | 22.01 | 117.17 | 108.30 |
| 5.00 | 19.61 | 137.98 | 111.50 |
| 6.00 | 14.25 | 154.91 | 105.49 |
| 8.00 | 8.56 | 177.72 | 101.24 |
| 10.00 | 5.48 | 191.76 | 99.70 |
| 12.00 | 3.32 | 200.55 | 98.16 |
| 24.00 | 0.50 | 223.49 | 101.28 |

Elimination Constant = .1763 $HR^{-1}$

TABLE XV

Theophylline Plasma Concentrations, Area Under the Plasma Level/Time Curve and Percent Absorbed for Dog C After Administration of Formula I by Gastric Intubation

| Time Hours | Plasma Concentration MCG/ML | Cumulative A.U.C. | Percent Absorbed |
|---|---|---|---|
| 0.09 | 14.40 | 0.65 | 37.76 |
| 0.17 | 13.49 | 1.76 | 35.84 |
| 0.25 | 17.31 | 3.00 | 46.26 |
| 0.33 | 20.35 | 4.50 | 54.79 |
| 0.42 | 24.10 | 6.50 | 65.33 |
| 0.50 | 24.55 | 8.45 | 67.27 |
| 0.67 | 28.69 | 12.97 | 79.86 |
| 0.83 | 32.83 | 17.89 | 92.57 |
| 1.00 | 34.79 | 23.64 | 99.95 |
| 1.50 | 32.31 | 40.42 | 100.14 |
| 2.00 | 30.63 | 56.15 | 101.97 |
| 3.00 | 28.62 | 85.78 | 108.42 |
| 4.00 | 23.17 | 111.67 | 104.46 |
| 5.00 | 22.12 | 134.31 | 110.68 |
| 6.00 | 19.02 | 154.88 | 110.73 |
| 8.00 | 13.71 | 187.62 | 109.85 |
| 10.00 | 7.95 | 209.28 | 103.40 |
| 12.00 | 4.65 | 221.88 | 99.78 |
| 24.00 | 0.55 | 253.09 | 101.44 |

Elimination Constant = .1517 $HR^{-1}$

TABLE XVI

Theophylline Plasma Concentrations, Area Under the Plasma Level/Time Curve and Percent Absorbed for Dog D After Administration of Formula I by Gastric Intubation

| Time Hours | Plasma Concentration MCG/ML | Cumulative A.U.C. | Percent Absorbed |
|---|---|---|---|
| 0.25 | 5.59 | 0.70 | 11.38 |
| 0.50 | 12.08 | 2.91 | 25.14 |
| 0.75 | 24.17 | 7.44 | 50.93 |
| 1.00 | 29.97 | 14.21 | 65.15 |
| 1.50 | 31.20 | 29.50 | 73.68 |
| 2.00 | 31.87 | 45.27 | 81.27 |
| 2.50 | 30.03 | 60.74 | 83.79 |
| 3.00 | 27.91 | 75.23 | 85.34 |
| 4.00 | 24.85 | 101.61 | 89.76 |
| 6.00 | 18.90 | 145.36 | 95.37 |
| 8.00 | 12.40 | 176.66 | 94.91 |
| 10.00 | 8.28 | 197.34 | 94.98 |
| 12.00 | 5.36 | 210.98 | 94.60 |
| 25.60 | 0.57 | 251.27 | 101.12 |

Elimination Constant = .2005 $HR^{-1}$

TABLE XVII

Theophylline Plasma Concentrations, Area Under the Plasma Level/Time Curve and Percent Absorbed for Dog A After Administration of Formula II by Gastric Intubation

| Time Hours | Plasma Concentration MCG/ML | Cumulative A.U.C. | Percent Absorbed |
|---|---|---|---|
| 0.08 | 2.42 | 0.10 | 6.69 |
| 0.17 | 12.89 | 0.79 | 35.70 |
| 0.25 | 19.87 | 2.10 | 55.38 |
| 0.33 | 22.05 | 3.77 | 62.01 |
| 0.42 | 23.52 | 5.82 | 66.85 |
| 0.50 | 24.75 | 7.75 | 70.98 |
| 0.67 | 25.20 | 12.00 | 73.84 |
| 0.83 | 26.84 | 16.16 | 79.97 |
| 1.00 | 27.33 | 20.77 | 83.08 |
| 1.60 | 32.08 | 38.59 | 103.02 |
| 2.07 | 34.15 | 54.15 | 114.73 |
| 3.00 | 33.27 | 85.50 | 124.43 |
| 4.00 | 28.22 | 116.24 | 122.47 |
| 5.00 | 23.09 | 141.90 | 118.28 |
| 6.00 | 19.33 | 163.11 | 116.16 |
| 8.00 | 11.36 | 193.80 | 106.15 |

TABLE XVII-continued

Theophylline Plasma Concentrations, Area Under the Plasma Level/Time Curve and Percent Absorbed for Dog A After Administration of Formula II by Gastric Intubation

| Time Hours | Plasma Concentration MCG/ML | Cumulative A.U.C. | Percent Absorbed |
|---|---|---|---|
| 10.00 | 7.20 | 212.37 | 101.90 |
| 12.00 | 4.80 | 224.36 | 99.94 |
| 24.00 | 0.91 | 258.60 | 102.49 |

Elimination Constant = .1408 $HR^{-1}$

TABLE XVIII

Theophylline Plasma Concentrations, Area Under the Plasma Level/Time Curve and Percent Absorbed for Dog B After Administration of Formula II by Gastric Intubation

| Time Hours | Plasma Concentration MCG/ML | Cumulative A.U.C. | Percent Absorbed |
|---|---|---|---|
| 0.08 | 0.43 | 0.02 | 0.96 |
| 0.17 | 1.32 | 0.10 | 2.95 |
| 0.25 | 24.27 | 1.12 | 53.85 |
| 0.33 | 31.80 | 3.36 | 71.31 |
| 0.42 | 32.20 | 6.24 | 73.30 |
| 0.50 | 35.15 | 8.94 | 80.84 |
| 0.67 | 37.11 | 15.08 | 87.53 |
| 0.83 | 39.23 | 21.19 | 94.56 |
| 1.00 | 39.36 | 27.87 | 97.44 |
| 1.50 | 39.31 | 47.53 | 104.96 |
| 2.00 | 36.96 | 66.60 | 107.19 |
| 3.00 | 29.79 | 99.97 | 104.37 |
| 4.00 | 24.46 | 127.10 | 103.17 |
| 5.00 | 20.74 | 149.70 | 103.73 |
| 6.00 | 17.69 | 168.91 | 104.48 |
| 8.00 | 11.93 | 198.53 | 103.29 |
| 10.00 | 5.65 | 216.10 | 96.29 |
| 12.00 | 3.98 | 225.73 | 96.36 |
| 24.00 | 1.34 | 257.70 | 102.96 |

Elimination Constant = .1763 $HR^{-1}$

TABLE XIX

Theophylline Plasma Concentrations, Area Under the Plasma Level/Time Curve and Percent Absorbed for Dog C After Administration of Formula II by Gastric Intubation

| Time Hours | Plasma Concentration MCG/ML | Cumulative A.U.C. | Percent Absorbed |
|---|---|---|---|
| 0.08 | 0.80 | 0.03 | 1.67 |
| 0.17 | 2.82 | 0.20 | 5.86 |
| 0.25 | 5.95 | 0.55 | 12.42 |
| 0.33 | 14.99 | 1.38 | 31.28 |
| 0.42 | 24.05 | 3.14 | 50.48 |
| 0.50 | 23.32 | 5.04 | 49.57 |
| 0.67 | 26.89 | 9.30 | 58.25 |
| 0.83 | 30.68 | 13.91 | 67.49 |
| 1.00 | 34.91 | 19.49 | 77.94 |
| 1.50 | 39.85 | 38.18 | 93.94 |
| 2.00 | 40.65 | 58.30 | 101.86 |
| 3.00 | 37.40 | 97.33 | 107.36 |
| 4.00 | 32.33 | 132.19 | 107.81 |
| 5.00 | 27.34 | 162.03 | 106.86 |
| 6.00 | 23.62 | 187.51 | 107.15 |
| 8.00 | 16.09 | 227.21 | 104.04 |
| 10.00 | 10.91 | 254.21 | 101.82 |
| 12.00 | 7.44 | 272.55 | 100.40 |
| 24.00 | 0.52 | 320.00 | 101.07 |

Elimination Constant = .1517

TABLE XX

Theophylline Plasma Concentrations, Area Under the Plasma Level/Time Curve and Percent Absorbed for Dog A After Administration of Formula III by Gastric Intubation

| Time Hours | Plasma Concentration MCG/ML | Cumulative A.U.C. | Percent Absorbed |
|---|---|---|---|
| 0.08 | 0.52 | 0.02 | 1.05 |
| 0.17 | 4.13 | 0.23 | 8.26 |
| 0.25 | 10.53 | 0.82 | 21.12 |
| 0.38 | 20.12 | 2.81 | 40.70 |
| 0.50 | 22.25 | 5.35 | 45.65 |
| 0.67 | 26.42 | 9.49 | 55.07 |
| 0.83 | 27.79 | 13.83 | 58.99 |
| 1.00 | 31.20 | 18.84 | 67.17 |
| 1.50 | 38.81 | 36.34 | 87.14 |
| 2.00 | 41.75 | 56.48 | 98.61 |
| 3.00 | 42.62 | 98.67 | 112.12 |
| 4.00 | 38.10 | 139.03 | 114.42 |
| 5.00 | 33.11 | 174.63 | 114.47 |
| 6.00 | 28.65 | 205.51 | 114.24 |
| 8.17 | 18.68 | 256.86 | 108.81 |
| 10.00 | 12.25 | 285.16 | 103.96 |
| 12.00 | 7.30 | 304.70 | 99.59 |
| 24.00 | 1.58 | 357.99 | 103.14 |

Elimination Constant = .1408 HR$^{-1}$

TABLE XXI

Theophylline Plasma Concentrations, Area Under the Plasma Level/Time Curve and Percent Absorbed for Dog B After Administration of Formula III by Gastric Intubation

| Time Hours | Plasma Concentration MCG/ML | Cumulative A.U.C. | Percent Absorbed |
|---|---|---|---|
| 0.08 | 0.56 | 0.02 | 0.89 |
| 0.17 | 3.60 | 0.21 | 5.71 |
| 0.25 | 7.79 | 0.67 | 12.44 |
| 0.33 | 10.43 | 1.39 | 16.79 |
| 0.42 | 16.81 | 2.62 | 27.17 |
| 0.50 | 32.31 | 4.59 | 52.08 |
| 0.67 | 43.32 | 11.01 | 71.17 |
| 0.83 | 49.11 | 18.41 | 82.33 |
| 1.00 | 48.63 | 26.72 | 83.88 |
| 1.50 | 54.60 | 52.52 | 100.42 |
| 2.00 | 52.34 | 79.26 | 104.28 |
| 3.00 | 43.93 | 127.40 | 104.40 |
| 4.00 | 37.42 | 168.07 | 105.43 |
| 5.00 | 30.86 | 202.21 | 104.59 |
| 6.00 | 25.89 | 230.59 | 104.65 |
| 8.00 | 15.56 | 272.04 | 99.88 |
| 10.00 | 9.56 | 297.15 | 97.41 |
| 12.00 | 6.28 | 312.98 | 96.64 |
| 24.00 | 1.68 | 360.71 | 102.64 |

Elimination Constant = .1763 HR$^{-1}$

TABLE XXII

Theophylline Plasma Concentrations, Area Under the Plasma Level/Time Curve and Percent Absorbed for Dog C After Administration of Formula III by Gastric Intubation

| Time Hours | Plasma Concentration MCG/ML | Cumulative A.U.C. | Percent Absorbed |
|---|---|---|---|
| 0.08 | 1.60 | 0.06 | 3.48 |
| 0.17 | 3.79 | 0.31 | 8.29 |
| 0.25 | 25.26 | 1.47 | 55.10 |
| 0.33 | 45.95 | 4.32 | 100.80 |
| 0.43 | 44.56 | 8.84 | 99.26 |
| 0.52 | 44.98 | 12.87 | 101.49 |
| 0.67 | 45.04 | 19.62 | 103.84 |
| 0.83 | 45.28 | 26.85 | 106.75 |
| 1.00 | 44.18 | 34.45 | 106.84 |
| 1.50 | 39.59 | 55.39 | 103.79 |
| 2.00 | 41.43 | 75.65 | 114.43 |
| 3.00 | 36.86 | 114.79 | 117.37 |
| 4.00 | 32.94 | 149.69 | 120.36 |
| 5.00 | 27.63 | 179.98 | 118.80 |
| 6.00 | 23.43 | 205.51 | 118.09 |
| 8.00 | 12.31 | 241.24 | 105.77 |
| 10.00 | 8.21 | 261.77 | 103.64 |
| 12.00 | 4.39 | 274.37 | 99.52 |
| 24.00 | 0.68 | 304.80 | 101.47 |

Elimination Constant = .1517

TABLE XXIII

Theophylline Plasma Concentrations, Area Under the Plasma Level/Time Curve and Percent Absorbed for Dog A After Administration of Formula IV by Gastric Intubation

| Time Hours | Plasma Concentration MCG/ML | Cumulative A.U.C. | Percent Absorbed |
|---|---|---|---|
| 0.09 | 0.92 | 0.04 | 1.94 |
| 0.18 | 0.83 | 0.12 | 1.77 |
| 0.26 | 2.32 | 0.25 | 4.92 |
| 0.33 | 4.20 | 0.47 | 8.91 |
| 0.42 | 5.40 | 0.91 | 11.54 |
| 0.51 | 6.86 | 1.46 | 14.75 |
| 0.67 | 10.36 | 2.84 | 22.46 |
| 0.84 | 14.13 | 4.92 | 30.94 |
| 1.00 | 17.27 | 7.43 | 38.23 |
| 1.50 | 26.97 | 18.49 | 61.74 |
| 2.00 | 34.31 | 33.81 | 81.56 |
| 3.00 | 41.20 | 71.57 | 107.04 |
| 4.00 | 38.70 | 111.52 | 113.56 |
| 5.00 | 31.72 | 146.73 | 109.33 |
| 6.00 | 26.53 | 175.85 | 107.07 |
| 8.00 | 17.51 | 219.89 | 101.17 |
| 10.00 | 13.13 | 250.53 | 101.04 |
| 12.00 | 9.19 | 272.85 | 99.37 |
| 24.00 | 2.04 | 340.25 | 104.27 |

Elimination Constant = .1408 HR$^{-1}$

TABLE XXIV

Theophylline Plasma Concentrations, Area Under the Plasma Level/Time Curve and Percent Absorbed for Dog B After Administration of Formula IV by Gastric Intubation

| Time Hours | Plasma Concentration MCG/ML | Cumulative A.U.C. | Percent Absorbed |
|---|---|---|---|
| 0.09 | 3.05 | 0.14 | 5.51 |
| 0.17 | 19.40 | 1.04 | 35.13 |
| 0.25 | 26.07 | 2.85 | 47.67 |
| 0.33 | 30.35 | 5.11 | 56.06 |
| 0.42 | 35.69 | 8.08 | 66.57 |
| 0.50 | 40.32 | 11.12 | 75.84 |
| 0.67 | 42.17 | 18.13 | 81.37 |
| 0.86 | 44.55 | 26.37 | 88.25 |
| 1.00 | 45.05 | 32.64 | 91.13 |
| 1.50 | 46.18 | 55.45 | 100.37 |
| 2.00 | 42.80 | 77.70 | 101.35 |
| 3.00 | 36.76 | 117.47 | 103.08 |
| 4.00 | 30.92 | 151.31 | 103.31 |
| 5.00 | 26.69 | 180.11 | 104.83 |
| 6.00 | 22.31 | 204.61 | 104.73 |
| 8.00 | 14.43 | 241.36 | 102.21 |
| 10.00 | 8.32 | 264.11 | 98.46 |
| 12.00 | 5.35 | 277.79 | 97.44 |
| 25.00 | 0.56 | 316.21 | 101.01 |

Elimination Constant = .1763 HR$^{-1}$

TABLE XXV

Theophylline Plasma Concentrations, Area Under the Plasma Level/Time Curve and Percent Absorbed for Dog C After Administration of Formula IV by Gastric Intubation

| Time Hours | Plasma Concentration MCG/ML | Cumulative A.U.C. | Percent Absorbed |
|---|---|---|---|
| 0.08 | 0.45 | 0.02 | 0.94 |
| 0.17 | 0.77 | 0.07 | 1.61 |
| 0.25 | 3.34 | 0.24 | 6.96 |
| 0.33 | 5.65 | 0.60 | 11.84 |
| 0.42 | 6.75 | 1.15 | 14.28 |
| 0.50 | 7.92 | 1.74 | 16.88 |
| 0.67 | 11.45 | 3.39 | 24.68 |
| 0.83 | 17.70 | 5.72 | 38.29 |
| 1.00 | 23.73 | 9.24 | 51.83 |
| 1.50 | 36.87 | 24.39 | 83.68 |
| 2.00 | 40.00 | 43.83 | 98.07 |
| 3.00 | 41.92 | 85.24 | 113.15 |
| 4.00 | 35.51 | 123.96 | 112.02 |
| 5.00 | 31.52 | 157.47 | 114.29 |
| 6.00 | 24.98 | 185.72 | 109.63 |
| 8.00 | 17.17 | 227.87 | 106.72 |
| 10.00 | 10.89 | 255.93 | 102.54 |
| 12.00 | 6.92 | 273.74 | 99.93 |
| 24.00 | 0.72 | 319.59 | 101.48 |

Elimination Constant = .1517

TABLE XXVI

Theophylline Plasma Concentrations, Area Under the Plasma Level/Time Curve and Percent Absorbed for Dog A After Administration of Formula V by Capsule

| Time Hours | Plasma Concentration MCG/ML | Cumulative A.U.C. | Percent Absorbed |
|---|---|---|---|
| 0.25 | 2.44 | 0.31 | 9.08 |
| 0.50 | 4.63 | 1.19 | 17.49 |
| 0.75 | 5.73 | 2.48 | 22.17 |
| 1.00 | 7.42 | 4.13 | 29.20 |
| 1.50 | 10.82 | 8.69 | 43.94 |
| 2.00 | 20.83 | 16.60 | 84.55 |
| 2.50 | 23.11 | 27.58 | 98.49 |
| 3.00 | 26.98 | 40.10 | 119.07 |
| 4.00 | 22.64 | 64.91 | 115.98 |
| 6.00 | 17.42 | 104.97 | 117.52 |
| 8.00 | 10.69 | 133.08 | 107.40 |
| 10.00 | 7.37 | 151.14 | 104.55 |
| 12.00 | 4.54 | 163.05 | 100.35 |
| 24.00 | 0.72 | 194.61 | 102.63 |

Elimination Constant = .1408 HR$^{-1}$

TABLE XXVII

Theophylline Plasma Concentrations, Area Under the Plasma Level/Time Curve and Percent Absorbed for Dog B After Administration of Formula V by Capsule

| Time Hours | Plasma Concentration MCG/ML | Cumulative A.U.C. | Percent Absorbed |
|---|---|---|---|
| 0.25 | 2.21 | 0.28 | 8.82 |
| 0.77 | 7.35 | 2.75 | 30.64 |
| 1.00 | 11.63 | 4.96 | 48.89 |
| 1.50 | 16.37 | 11.96 | 72.21 |
| 2.00 | 16.15 | 20.09 | 76.96 |
| 2.50 | 15.85 | 28.09 | 81.32 |
| 3.00 | 15.06 | 35.82 | 83.56 |
| 4.00 | 13.43 | 50.06 | 86.98 |
| 6.00 | 11.18 | 74.67 | 95.15 |
| 8.00 | 10.15 | 96.00 | 105.85 |
| 10.00 | 5.70 | 111.86 | 99.35 |
| 12.00 | 3.43 | 120.99 | 96.78 |
| 24.30 | 0.49 | 145.12 | 101.93 |

Elimination Constant = .1763 HR$^{-1}$

TABLE XXVIII

Theophylline Plasma Concentrations, Area Under the Plasma Level/Time Curve and Percent Absorbed for Dog C After Administration of Formula V by Capsule

| Time Hours | Plasma Concentration MCG/ML | Cumulative A.U.C. | Percent Absorbed |
|---|---|---|---|
| 0.25 | 0.65 | 0.08 | 2.93 |
| 0.50 | 1.10 | 0.30 | 5.11 |
| 0.75 | 2.75 | 0.78 | 12.79 |
| 1.00 | 3.79 | 1.60 | 17.97 |
| 1.50 | 7.20 | 4.34 | 35.02 |
| 2.00 | 8.86 | 8.36 | 45.14 |
| 2.50 | 10.88 | 13.29 | 57.49 |
| 3.00 | 11.37 | 18.85 | 63.42 |
| 4.00 | 12.10 | 30.59 | 74.61 |
| 6.00 | 15.91 | 58.59 | 110.53 |
| 8.00 | 10.37 | 84.87 | 103.63 |
| 10.00 | 7.32 | 102.57 | 102.01 |
| 12.00 | 4.58 | 114.47 | 97.84 |
| 24.00 | 0.98 | 147.87 | 104.39 |

Elimination constant = .1517 HR$^{-1}$

TABLE XXIX

Theophylline Plasma Concentrations, Area Under the Plasma Level/Time Curve and Percent Absorbed for Dog D After Administration of Formula V by Capsule

| Time Hours | Plasma Concentration MCG/ML | Cumulative A.U.C. | Percent Absorbed |
|---|---|---|---|
| 0.25 | 2.38 | 0.30 | 6.21 |
| 0.50 | 4.77 | 1.19 | 12.76 |
| 0.75 | 7.25 | 2.69 | 19.83 |
| 1.00 | 9.59 | 4.80 | 26.85 |
| 1.50 | 12.47 | 10.31 | 36.99 |
| 2.00 | 14.13 | 16.96 | 44.62 |
| 2.50 | 14.30 | 24.07 | 48.67 |
| 3.00 | 15.66 | 31.56 | 55.97 |
| 4.00 | 15.58 | 47.18 | 63.73 |
| 6.00 | 17.09 | 79.85 | 84.25 |
| 8.00 | 14.54 | 111.49 | 93.90 |
| 10.00 | 8.92 | 134.95 | 91.57 |
| 12.00 | 6.75 | 150.63 | 94.05 |
| 24.00 | 0.80 | 195.97 | 102.05 |

Elimination Constant = .2005 HR$^{-1}$

TABLE XXX

Theophylline Plasma Concentrations, Area Under the Plasma Level/Time Curve and Percent Absorbed for Dog A After Administration of Formula VI by Capsule

| Time Hours | Plasma Concentration MCG/ML | Cumulative A.U.C. | Percent Absorbed |
|---|---|---|---|
| 0.30 | 12.00 | 1.80 | 48.42 |
| 0.50 | 13.74 | 4.37 | 56.70 |
| 0.75 | 15.39 | 8.01 | 65.27 |
| 1.00 | 16.56 | 12.01 | 72.11 |
| 1.70 | 19.35 | 24.58 | 90.10 |
| 2.00 | 19.48 | 30.40 | 93.88 |
| 2.50 | 19.76 | 40.21 | 100.42 |
| 3.00 | 19.42 | 50.01 | 104.56 |
| 4.00 | 18.55 | 68.99 | 111.65 |
| 6.00 | 14.44 | 101.98 | 113.76 |
| 8.00 | 8.88 | 125.30 | 104.80 |
| 10.00 | 6.49 | 140.67 | 103.88 |
| 12.00 | 4.21 | 151.37 | 100.82 |
| 24.00 | 0.53 | 179.77 | 102.08 |

Elimination Constant = .1408 HR$^{-1}$

TABLE XXXI

Theophylline Plasma Concentrations, Area Under the Plasma Level/Time Curve and Percent Absorbed for Dog D After Administration of Formula VI by Capsule

| Time Hours | Plasma Concentration MCG/ML | Cumulative A.U.C. | Percent Absorbed |
|---|---|---|---|
| 0.30 | 2.19 | 0.33 | 6.96 |
| 0.50 | 2.89 | 0.84 | 9.47 |
| 0.78 | 3.94 | 1.80 | 13.29 |
| 1.00 | 5.47 | 2.82 | 18.67 |
| 1.50 | 11.15 | 6.98 | 38.78 |
| 2.00 | 14.51 | 13.39 | 53.17 |
| 2.50 | 15.32 | 20.85 | 60.29 |
| 3.00 | 15.36 | 28.52 | 65.16 |
| 4.00 | 15.06 | 43.74 | 73.68 |
| 6.00 | 13.37 | 72.17 | 86.07 |
| 8.00 | 10.50 | 96.04 | 91.97 |
| 10.00 | 7.05 | 113.59 | 92.19 |
| 12.00 | 4.90 | 125.54 | 92.97 |
| 24.00 | 1.06 | 161.34 | 103.29 |

Elimination Constant = .2005 $HR^{-1}$

TABLE XXXII

Theophylline Plasma Concentrations, Area Under the Plasma Level/Time Curve and Percent Absorbed for Dog A After Administration of Formula VII by Capsule

| Time Hours | Plasma Concentration MCG/ML | Cumulative A.U.C. | Percent Absorbed |
|---|---|---|---|
| 0.25 | 1.30 | 0.16 | 4.48 |
| 0.50 | 4.35 | 0.87 | 15.10 |
| 0.75 | 7.40 | 2.34 | 26.11 |
| 1.10 | 9.52 | 5.30 | 34.67 |
| 1.50 | 13.12 | 9.82 | 48.99 |
| 2.10 | 14.40 | 18.08 | 57.24 |
| 2.50 | 14.88 | 23.93 | 61.65 |
| 3.00 | 21.91 | 33.13 | 89.78 |
| 4.00 | 25.55 | 56.86 | 113.38 |
| 6.00 | 19.83 | 102.24 | 115.61 |
| 8.00 | 12.52 | 134.58 | 106.30 |
| 10.00 | 8.41 | 155.51 | 102.40 |
| 12.00 | 5.65 | 169.58 | 99.75 |
| 24.00 | 1.13 | 210.23 | 103.80 |

Elimination Constant = .1408 $HR^{-1}$

TABLE XXXIII

Theophylline Plasma Concentrations, Area Under the Plasma Level/Time Curve and Percent Absorbed for Dog B After Administration of Formula VII by Capsule

| Time Hours | Plasma Concentration MCG/ML | Cumulative A.U.C. | Percent Absorbed |
|---|---|---|---|
| 0.25 | 31.05 | 3.88 | 98.70 |
| 0.50 | 25.46 | 10.95 | 85.20 |
| 0.80 | 24.37 | 18.42 | 85.91 |
| 1.00 | 23.96 | 23.25 | 87.27 |
| 1.50 | 21.05 | 34.51 | 84.39 |
| 2.00 | 22.09 | 45.29 | 93.53 |
| 2.50 | 20.87 | 56.03 | 95.64 |
| 3.00 | 19.64 | 66.16 | 97.38 |
| 4.00 | 17.19 | 84.58 | 99.85 |
| 6.00 | 11.46 | 113.23 | 97.74 |
| 8.00 | 7.22 | 131.91 | 94.81 |
| 10.00 | 5.26 | 144.40 | 95.55 |
| 12.00 | 3.60 | 153.26 | 95.24 |
| 24.00 | 1.25 | 182.36 | 103.88 |

Elimination Constant = .1763 $HR^{-1}$

TABLE XXXIV

Theophylline Plasma Concentrations, Area Under the Plasma Level/Time Curve and Percent Absorbed for Dog C After Administration of Formula VII by Capsule

| Time Hours | Plasma Concentration MCG/ML | Cumulative A.U.C. | Percent Absorbed |
|---|---|---|---|
| 0.23 | 1.52 | 0.17 | 6.60 |
| 0.52 | 4.59 | 1.06 | 20.34 |
| 0.80 | 6.64 | 2.63 | 30.13 |
| 1.00 | 9.03 | 4.20 | 41.35 |
| 1.50 | 12.85 | 9.67 | 61.26 |
| 2.00 | 15.07 | 16.65 | 75.28 |
| 2.50 | 15.29 | 24.24 | 81.16 |
| 3.00 | 18.26 | 32.63 | 99.29 |
| 4.00 | 17.72 | 50.62 | 108.68 |
| 6.00 | 13.00 | 81.34 | 108.39 |
| 8.00 | 7.48 | 101.82 | 98.08 |
| 10.00 | 4.68 | 113.98 | 94.00 |
| 12.00 | 3.72 | 122.38 | 95.35 |
| 24.00 | 1.56 | 154.08 | 106.68 |

Elimination Constant = .1517 $HR^{-1}$

TABLE XXXV

Theophylline Plasma Concentrations, Area Under the Plasma Level/Time Curve and Percent Absorbed for Dog D After Administration of Formula VII by Capsule

| Time Hours | Plasma Concentration MCG/ML | Cumulative A.U.C. | Percent Absorbed |
|---|---|---|---|
| 0.25 | 9.34 | 1.17 | 23.59 |
| 0.50 | 11.58 | 3.78 | 30.40 |
| 0.83 | 14.16 | 8.03 | 38.85 |
| 1.00 | 14.44 | 10.46 | 40.73 |
| 1.50 | 15.19 | 17.87 | 46.23 |
| 2.00 | 18.91 | 26.39 | 59.61 |
| 2.50 | 21.27 | 36.44 | 70.40 |
| 3.00 | 22.81 | 47.46 | 79.63 |
| 4.00 | 21.45 | 69.59 | 87.21 |
| 6.00 | 16.42 | 107.47 | 93.53 |
| 8.00 | 11.09 | 134.99 | 93.99 |
| 10.00 | 7.45 | 153.53 | 94.17 |
| 12.00 | 5.32 | 166.30 | 95.23 |
| 24.00 | 0.71 | 202.49 | 101.76 |

Elimination Constant = .2005 $HR^{-1}$

TABLE XXXVI

Theophylline Plasma Concentrations, Area Under the Plasma Level/Time Curve and Percent Absorbed for Dog A After Administration of Formula VIII by Capsule

| Time Hours | Plasma Concentration MCG/ML | Cumulative A.U.C. | Percent Absorbed |
|---|---|---|---|
| 0.28 | 2.24 | 0.31 | 8.88 |
| 0.50 | 3.52 | 0.95 | 14.21 |
| 0.75 | 4.20 | 1.91 | 17.38 |
| 1.00 | 6.82 | 3.29 | 28.32 |
| 1.50 | 10.48 | 7.61 | 44.93 |
| 2.00 | 13.87 | 13.70 | 61.48 |
| 2.50 | 15.55 | 21.06 | 72.05 |
| 3.00 | 17.33 | 29.28 | 83.47 |
| 4.00 | 18.57 | 47.23 | 98.13 |
| 6.00 | 18.35 | 84.16 | 117.50 |
| 8.00 | 11.64 | 114.14 | 107.79 |
| 10.00 | 7.46 | 133.23 | 101.99 |
| 12.00 | 5.52 | 146.21 | 101.56 |
| 24.00 | 0.54 | 182.55 | 102.10 |

Elimination Constant = .1408 $HR^{-1}$

TABLE XXXVII

Theophylline Plasma Concentrations, Area Under the Plasma Level/Time Curve and Percent Absorbed for Dog B After Administration of Formula VIII by Capsule

| Time Hours | Plasma Concentration MCG/ML | Cumulative A.U.C. | Percent Absorbed |
|---|---|---|---|
| 0.25 | 24.33 | 3.04 | 71.21 |
| 0.53 | 29.83 | 10.62 | 90.80 |
| 0.75 | 30.61 | 17.27 | 96.39 |
| 1.00 | 28.49 | 24.66 | 94.05 |
| 1.50 | 26.97 | 38.52 | 96.69 |
| 2.00 | 24.91 | 51.49 | 97.34 |
| 2.50 | 21.99 | 63.21 | 94.89 |
| 3.00 | 21.40 | 74.06 | 98.71 |
| 4.00 | 18.20 | 93.86 | 99.54 |
| 6.00 | 12.06 | 124.13 | 97.24 |
| 8.00 | 8.68 | 144.87 | 98.03 |
| 10.00 | 5.34 | 158.90 | 95.54 |
| 12.00 | 3.78 | 168.02 | 95.68 |
| 24.00 | 1.22 | 198.03 | 103.50 |

Elimination Constant = .1763 $HR^{-1}$

TABLE XXXVIII

Theophylline Plasma Concentrations, Area Under the Plasma Level/Time Curve and Percent Absorbed for Dog C After Administration of Formula VIII by Capsule

| Time Hours | Plasma Concentration MCG/ML | Cumulative A.U.C. | Percent Absorbed |
|---|---|---|---|
| 0.25 | 11.86 | 1.48 | 57.05 |
| 0.55 | 14.76 | 5.48 | 73.60 |
| 0.75 | 16.36 | 8.59 | 83.38 |
| 1.00 | 17.28 | 12.79 | 90.73 |
| 1.50 | 18.58 | 21.76 | 103.29 |
| 2.00 | 18.14 | 30.94 | 107.79 |
| 2.50 | 16.84 | 39.68 | 107.91 |
| 3.00 | 16.80 | 48.09 | 113.75 |
| 4.00 | 14.86 | 63.92 | 115.92 |
| 6.00 | 10.72 | 89.50 | 114.70 |
| 8.00 | 4.74 | 104.96 | 97.54 |
| 10.00 | 4.10 | 113.80 | 100.85 |
| 12.00 | 2.78 | 120.68 | 99.55 |
| 24.00 | 0.38 | 139.64 | 101.79 |

Elimination Constant = .1517 $HR^{-1}$

TABLE XXXIX

Theophylline Plasma Concentrations, Area Under the Plasma Level/Time Curve and Percent Absorbed for Dog D After Administration of Formula VIII by Capsule

| Time Hours | Plasma Concentration MCG/ML | Cumulative A.U.C. | Percent Absorbed |
|---|---|---|---|
| 0.25 | 0.88 | 0.11 | 2.25 |
| 0.50 | 7.22 | 1.12 | 18.59 |
| 0.75 | 12.80 | 3.63 | 33.77 |
| 1.00 | 14.56 | 7.05 | 39.88 |
| 1.50 | 16.16 | 14.73 | 47.71 |
| 2.00 | 19.59 | 23.67 | 60.72 |
| 2.50 | 20.59 | 33.71 | 68.25 |
| 3.00 | 20.79 | 44.05 | 73.92 |
| 4.00 | 19.99 | 64.44 | 82.13 |
| 6.00 | 16.40 | 100.83 | 91.40 |
| 8.00 | 11.96 | 129.19 | 94.51 |
| 10.00 | 7.72 | 148.88 | 93.78 |
| 12.00 | 5.30 | 161.90 | 94.25 |
| 24.00 | 1.02 | 199.83 | 102.55 |

Elimination Constant = .2005 $HR^{-1}$

Generally, it is seen that absorption of theophylline was significantly delayed or prolonged at some time for all suspensions exept Formula II, containing gelatin and carrageenan and Formula VI containing sodium alginate and xanthan gum, although the latter includes one of two experiments which appears to have succeeded despite failure of the statistical test. For gelatin and carageenan suspensions, gastric emptying would solubilize the matrix, since higher pH values such as are found in the small bowel were found to speed release and matrix distribution in vitro at elevated pH. Another factor is that the hidden gastric tube end may have been inserted between opposed gastric walls, causing spreading and increased surface area of the suspensions. Furthermore, beagles generally demonstrate a high tendency to vomit which may explain some of the inconsistent in vivo results employing intubation techniques, as esophageal reflux sounds and coughing were sometimes noted, at which time the dogs jaws were normally held closed to prevent possible ejection of gastric contents.

Given the observed differences in theophylline plasma levels after dosing with trial suspensions and after the one percent solution, and the significant differences in absorption times, it is concluded that the trial suspensions were generally effective in prolonging the absorption of theophylline relative to the one percent solutions.

Thus, while the invention has been described with reference to certain preferred embodiments, those skilled in the art will realize that changes and modifications may be made thereto without departing from the full and intended scope of the appended claims.

We claim:

1. A method for the controlled release administration of a pharmaceutically active agent comprising orally introducing said agent to the body in a normally liquid formulation containing a solution or suspension vehicle selected from the group consisting essentially of xanthan gum, sodium alginate, gelatin, carrageenan, methylcellulose and mixtures thereof in an amount from about 0.3 to about 5.0 percent by weight which forms a semi-solid gel-like matrix in the environment of the stomach thereby controlling the release of said pharmaceutically active agent.

2. The method of claim 1 wherein said vehicle comprises from about 0.3 to about 3 percent xanthan gum by weight.

3. The method of claim 1 wherein said vehicle comprises from about 0.5 to about 3 percent sodium alginate by weight.

4. The method of claim 1 wherein said vehicle comprises from about 0.3 to about 1.5 percent by weight of each gelatin and carrageenan.

5. The method of claim 1 wherein said vehicle comprises from about 1 to about 3 weight percent of methylcellulose.

6. The method of claim 1 wherein said vehicle comprises about 2 percent methylcellulose and about 5 percent sodium chloride by weight.

7. The method of claim 1 wherein the formulation further comprises additional excipients selected from locust bean gum, salts, sugars, $Na_3PO_4$, $CaCO_3$ and $Ca_2HPO_4$.

8. The method of claim 1 wherein said pharmaceutically active agent comprises theophylline.

9. In a method for controlled release administration of a pharmaceutically active agent, the improvement comprising orally administering said agent to the body in a normally liquid formulation containing a solution or suspension vehicle selected from the group consisting essentially of xanthan gum, sodium alginate, gelatin, carrageenan, methylcellulose and mixtures thereof in an amount from about 0.3 to about 5.0 percent by weight which forms a semi-solid gel-like matrix in the environment of the stomach thereby controlling the release of said pharmaceutically active agent.

10. The method of claim 9 wherein said vehicle comprises from about 0.3 to about 3 percent xanthan gum by weight.

11. The method of claim 9 wherein said vehicle comprises from about 0.5 to about 3 percent sodium alginate by weight.

12. The method of claim 9 wherein said vehicle comprises from about 0.3 to about 1.5 percent by weight of each gelatin and carrageenan.

13. The method of claim 9 wherein said vehicle comprises from about 1 to about 3 weight percent of methylcellulose.

14. The method of claim 9 wherein said vehicle comprises about 2 percent methylcellulose and about 5 percent sodium chloride by weight.

15. The method of claim 9 wherein the formulation further comprises additional excipients selected from locust bean gum, salts, sugars, $Na_3PO_4$, $CaCO_3$ and $Ca_2HPO_4$.

16. The method of claim 9 wherein said pharmaceutically active agent comprises theophylline.

17. A controlled release pharmaceutical composition comprising a normally liquid formulation containing a solution or suspension vehicle selected from the group consisting essentially of xanthan gum, sodium alginate, gelatin, carrageenan, methylcellulose and mixtures thereof in an amount from about 0.3 to about 5.0 percent by weight and a pharmaceutically active agent, said vehicle forming a semi-solid gel-like matrix in the environment of the stomach thereby controlling the release of said pharmaceutically active agent.

18. The composition of claim 17 wherein the said vehicle comprises from about 0.3 to about 3 percent xanthan gum by weight.

19. The composition of claim 17 wherein said vehicle comprises from about 0.5 to about 3 percent sodium alginate by weight.

20. The composition of claim 17 wherein said vehicle comprises from about 0.3 to about 1.5 percent by weight of each gelatin and carrageenan.

21. The composition of claim 17 wherein said vehicle comprises from about 1 to about 3 weight percent of methylcellulose.

22. The composition of claim 17 wherein said vehicle comprises about 2 percent methylcellulose and about 5 percent sodium chloride by weight.

23. The composition of claim 17 wherein the formulation further comprises additional excipients selected from locust bean gum, salts, sugars, $Na_3PO_4$, $CaCO_3$ and $Ca_2HPO_4$.

24. The composition of claim 17 wherein said pharmaceutically active agent comprises theophylline.

* * * * *